(12) United States Patent
Cho et al.

(10) Patent No.: US 10,071,050 B2
(45) Date of Patent: Sep. 11, 2018

(54) COSMETIC COMPOSITION CONTAINING EXOSOMES EXTRACTED FROM STEM CELL FOR SKIN WHITENING, ANTIWRINKLE OR REGENERATION

(71) Applicant: EXOSTEMTECH CO., LTD., Ansan (KR)

(72) Inventors: Yong Woo Cho, Seongnam (KR); Ji Suk Choi, Ansan (KR); Eun Ji Kim, Ansan (KR); Hwa In Yoon, Seoul (KR); Jun Sung Kim, Busan (KR)

(73) Assignee: EXOSTEMTECH CO., LTD., Ansan (KR)

( * ) Notice: Subject to any disclaimer, the term of this patent is extended or adjusted under 35 U.S.C. 154(b) by 0 days.

(21) Appl. No.: 15/429,493

(22) Filed: Feb. 10, 2017

(65) Prior Publication Data
US 2017/0209365 A1    Jul. 27, 2017

Related U.S. Application Data

(63) Continuation of application No. PCT/KR2015/012013, filed on Nov. 9, 2015.

(30) Foreign Application Priority Data

| Nov. 7, 2014 | (KR) | 10-2014-0154410 |
| Jan. 8, 2015 | (KR) | 10-2015-0002660 |
| Sep. 23, 2015 | (KR) | 10-2015-0134689 |
| Sep. 30, 2015 | (KR) | 10-2015-0137635 |

(51) Int. Cl.

| A61K 8/64 | (2006.01) |
| A61K 8/98 | (2006.01) |
| A61Q 19/02 | (2006.01) |
| A61Q 19/08 | (2006.01) |
| A61K 35/35 | (2015.01) |
| A61K 8/02 | (2006.01) |

(52) U.S. Cl.
CPC ............ A61K 8/981 (2013.01); A61K 8/0216 (2013.01); A61K 35/35 (2013.01); A61Q 19/02 (2013.01); A61Q 19/08 (2013.01); *A61K 2800/74* (2013.01); *A61K 2800/805* (2013.01)

(58) Field of Classification Search
CPC ............ A61K 8/64; A61K 8/97; A61K 8/981
See application file for complete search history.

(56) References Cited

U.S. PATENT DOCUMENTS

| 2011/0014251 A1 | 1/2011 | Ray et al. |
| 2011/0064682 A1 | 3/2011 | Nam |
| 2012/0141433 A1 | 6/2012 | Tankovich et al. |
| 2013/0209528 A1* | 8/2013 | Levi ................ A61K 8/14 424/400 |
| 2015/0018750 A1 | 1/2015 | Ueda et al. |
| 2015/0023908 A1* | 1/2015 | Al-Qahtani ............ A61Q 19/08 424/85.2 |

FOREIGN PATENT DOCUMENTS

| CN | 103767985 | | 5/2014 |
| CN | 104 382 827 | * | 3/2015 |
| EP | 2687219 | A1 | 1/2014 |
| JP | 2001-523084 | | 11/2001 |
| JP | 2007-528706 | A | 10/2007 |
| KR | 10-0788632 | | 12/2007 |
| KR | 10-2008-0075387 | A | 8/2008 |
| KR | 10-2008-0082657 | A | 9/2008 |
| KR | 10-2009-0116659 | | 11/2009 |
| KR | 10-2011-0001830 | | 1/2011 |
| KR | 10-1047873 | | 7/2011 |
| KR | 10-2013-0009651 | A | 1/2013 |
| KR | 10-2013-0028012 | A | 3/2013 |
| KR | 10-2013-0030846 | | 3/2013 |
| KR | 10-2013-0061950 | | 6/2013 |
| KR | 10-1279812 | B1 | 6/2013 |
| KR | 10-2013-0072983 | A | 7/2013 |
| KR | 10-2013-0116552 | | 10/2013 |
| KR | 10-2014-0024310 | | 2/2014 |
| KR | 10-2014-0066456 | | 6/2014 |
| KR | 10-1524079 | | 6/2015 |
| WO | 2013118877 | A1 | 8/2013 |
| WO | WO 2013/150303 | | 10/2013 |
| WO | 2014013258 | A1 | 1/2014 |

OTHER PUBLICATIONS

International Search Report for PCT/KR2015/012013 filed Nov. 9, 2015.
Written Opinion for PCT/KR2015/012013 filed Nov. 9, 2015.
Yang, Seong Hyun, "Adipose Tissue Engineering using Exosomes Secreted During Adipogenic Differentiation of Human Adipose-Derived Stem Cells", Master's Thesis, Graduate School of Hanyang University. Aug. 1, 2015, pp. 1-47.
Byung-Soon Park et al., "Adipose-Derived Stem Cells and Their Secretory Factors as a Promising Therapy for Skin Aging", Dermatologic Surgery, Oct. 2008.
Masamitsu Konno et al., "Adipose-derived mesenchymal stem cells and regenerative medicine", The Japanese Society of Developmental Biologists, 2013, pp. 309-318.
Xiao Xu et al., "Adipose-derived stem cells cooperate with fractional carbon dioxide laser in antagonizing photoaging: a potential role of Wnt and β-catenin signaling", Cell & Bioscience, 2014.
Marie Maumus et al., "Mesenchymal stem cells in regenerative medicine applied to rheumatic diseases: role of secretome and exosomes", Biochimie, 2013, pp. 1-19.
International Search Report for PCT/KR2016/001230 filed Feb. 4, 2016.
Li Hu et al., "Effects of adipose stem cell-conditioned medium on the migration of vascular endothelial cells, fibroblasts and keratinocytes", Experimental and Therapeutic Medicine, Mar. 1, 2013, pp. 701-706, vol. 5, No. 3, Spandidos Publications.

(Continued)

*Primary Examiner* — Ruth A Davis

(57) ABSTRACT

A cosmetic composition for skin whitening, wrinkle improvement or skin regeneration includes, as an active ingredient, exosomes derived from stem cells comprising proliferating stem cells.

13 Claims, 41 Drawing Sheets

(56) References Cited

OTHER PUBLICATIONS

Li Hu et al., "Effects of adipose stem cell-conditioned medium on the migration of vascular endothelial cells, fibroblasts and keratinocytes", Experimental and Therapeutic Medicine, Sep. 16, 2016, p. 3137, vol. 12, No. 5.

* cited by examiner

[FIG. 1]
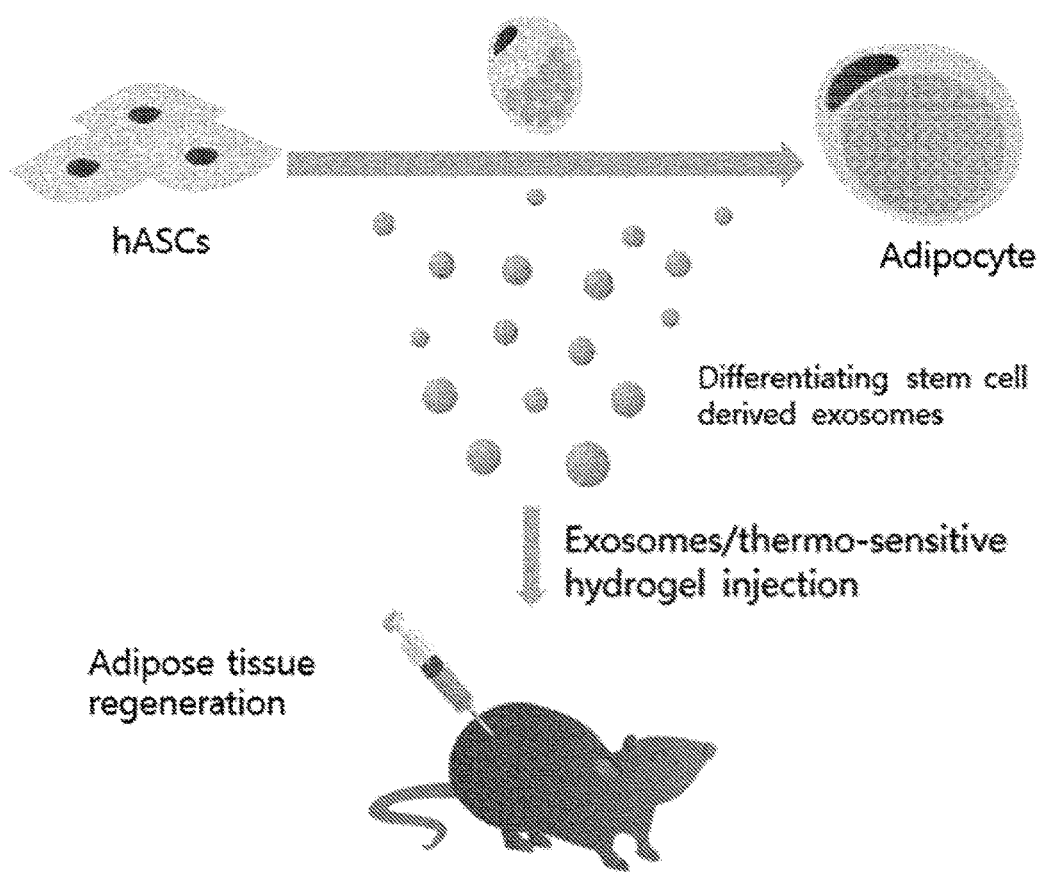

Cell culture supernatant

Centrifugation at 300xg, 4°C for 10min,
Collect supernatant

Supernatant

Centrifugation at 2,000xg, 4°C for 30min,
Collect supernatant

Supernatant

Filtration through
Amicon 3K
Centrifugation at 5,000xg, 4°C for 60min,
Collect supernatant

Supernatant

Mix exosome isolation
reagent(1 : 0.5)

1) After overnight,
   Centrifugation 10,000 xg , for 60min,
   Collect pellet
2) Exosome spin column

Exosomes

FIG. 2

[FIG. 3A]
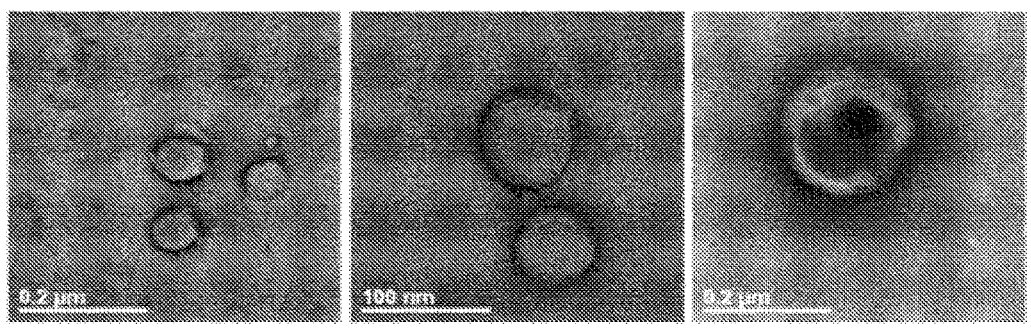
[FIG. 3B]
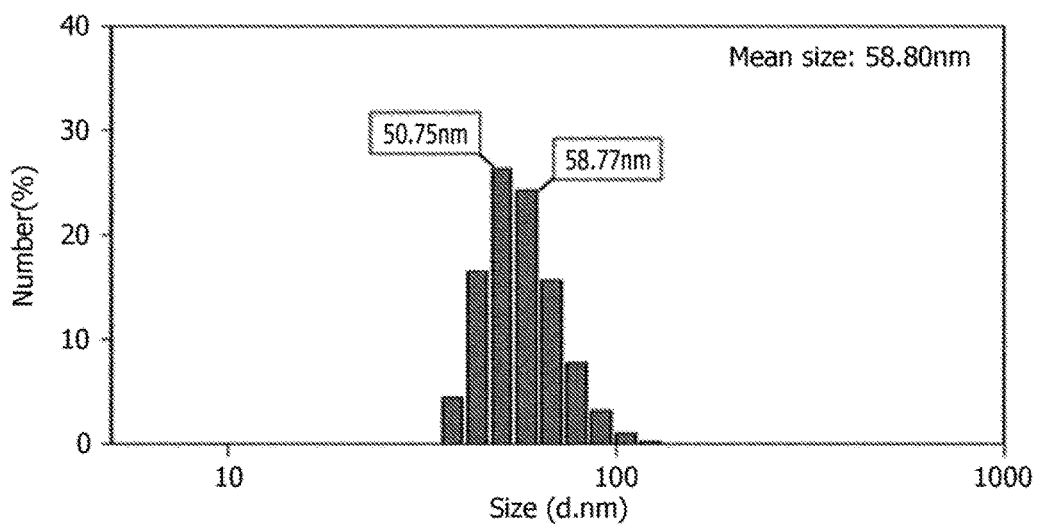

[FIG. 3C]
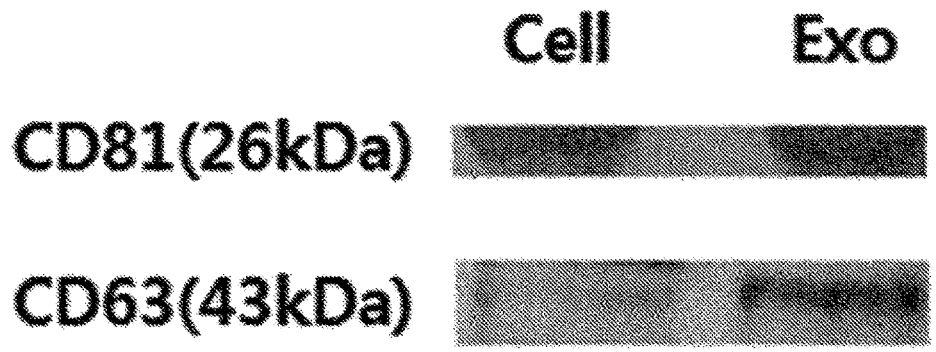
[FIG. 4A]
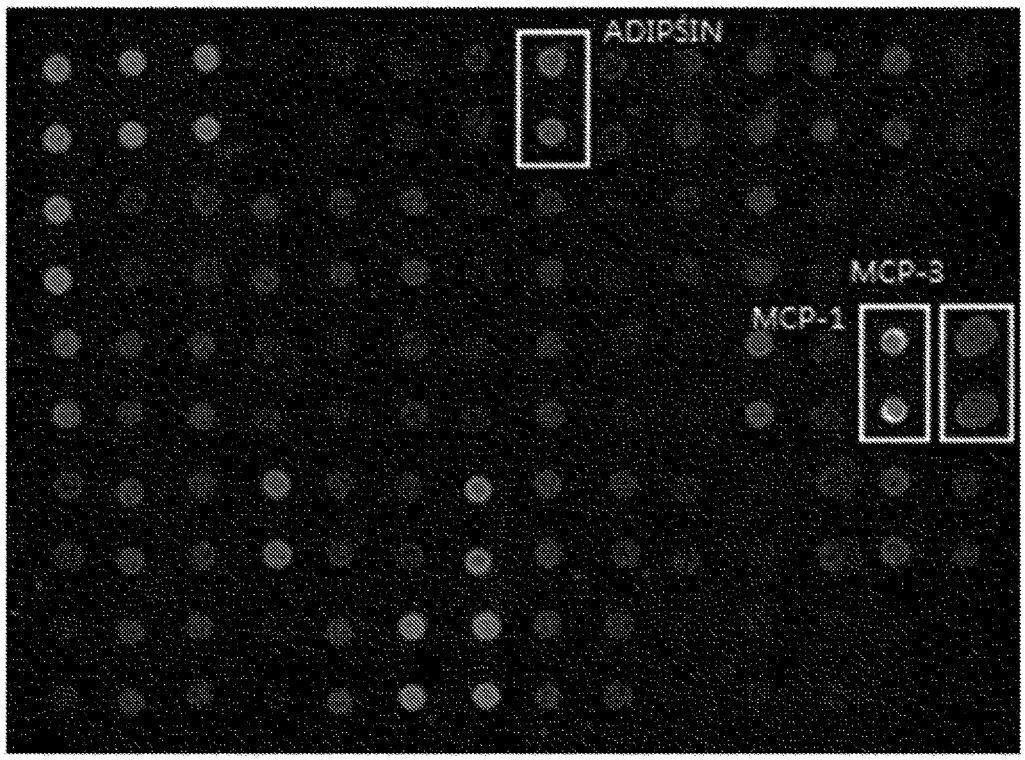

[FIG. 4B]

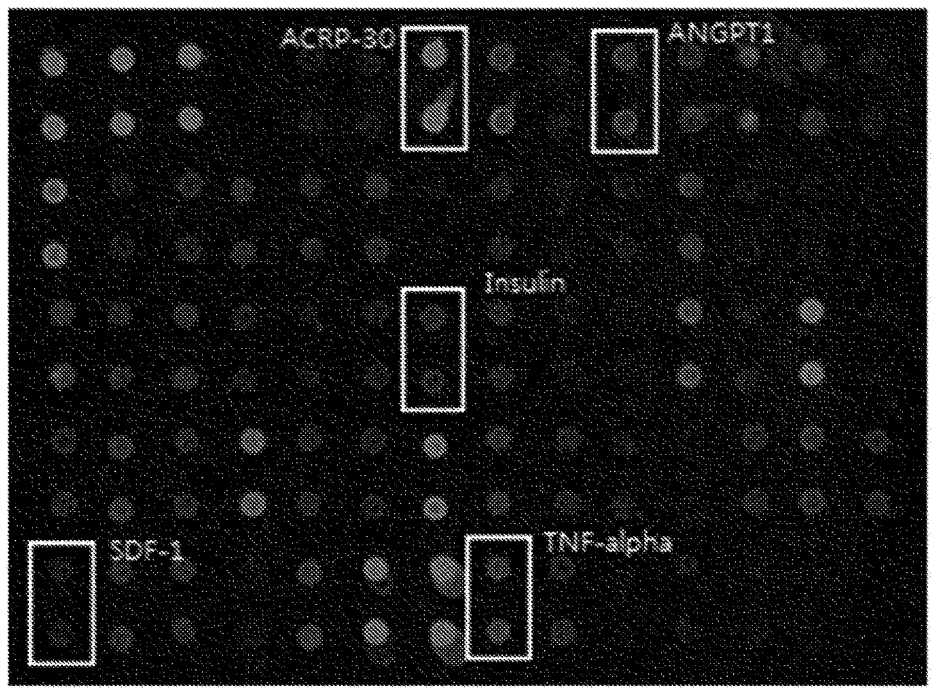

[FIG. 4C]

| POS1 | POS2 | POS3 | NEG | 4-1BB | ACE-2 | ACRP-30 | Adipsin | AgRP | ANGPT 1 | ANGPT 2 | ANGPT 4 | CRP | ENA-78 |
|---|---|---|---|---|---|---|---|---|---|---|---|---|---|
| POS1 | POS2 | POS3 | NEG | 4-1BB | ACE-2 | ACRP-30 | Adipsin | AgRP | ANGPT 1 | ANGPT 2 | ANGPT 4 | CRP | ENA-78 |
| Fas | FGF-6 | GH | HCC-4 | IFN-gamma | IGFBP-1 | IGFBP-2 | IGFBP-3 | IGF-I | IGF-I sR | IL-1 alpha | IL-1 beta | IL-1 sRI | IL-1 R4/ST2 |
| Fas | FGF-6 | GH | HCC-4 | IFN-gamma | IGFBP-1 | IGFBP-2 | IGFBP-3 | IGF-I | IGF-I sR | IL-1 alpha | IL-1 beta | IL-1 sRI | IL-1 R4/ST2 |
| IL-6 | IL-6 sR | IL-5 | IL-10 | IL-11 | IL-12 | Insulin | IP-10 | Leptin | Leptin R | LIF | Lymphot actin | MCP-1 | MCP-3 |
| IL-6 | IL-6 sR | IL-5 | IL-10 | IL-11 | IL-12 | Insulin | IP-10 | Leptin | Leptin R | LIF | Lymphot actin | MCP-1 | MCP-3 |
| MCSF | MIF | MIP-1 beta | MSP alpha | OPG | OSM | PAI-I | PARC | PDGF-AA | PDGF-AB | PDGF-BB | RANTES | Resistin | SAA |
| MCSF | MIF | MIP-1 beta | MSP alpha | OPG | OSM | PAI-I | PARC | PDGF-AA | PDGF-AB | PDGF-BB | RANTES | REsistin | SAA |
| SDF-1 | cTNF RI | cTNF RII | TECK | TGF-beta | TIMP-1 | TIMP-2 | TNF-alpha | VEGF | XEDAR | NEG | NEG | NEG | NEG |
| SDF-1 | cTNF RI | cTNF RII | TECK | TGF-beta | TIMP-1 | TIMP-2 | TNF-alpha | VEGF | XEDAR | NEG | NEG | NEG | NEG |

[FIG. 5]
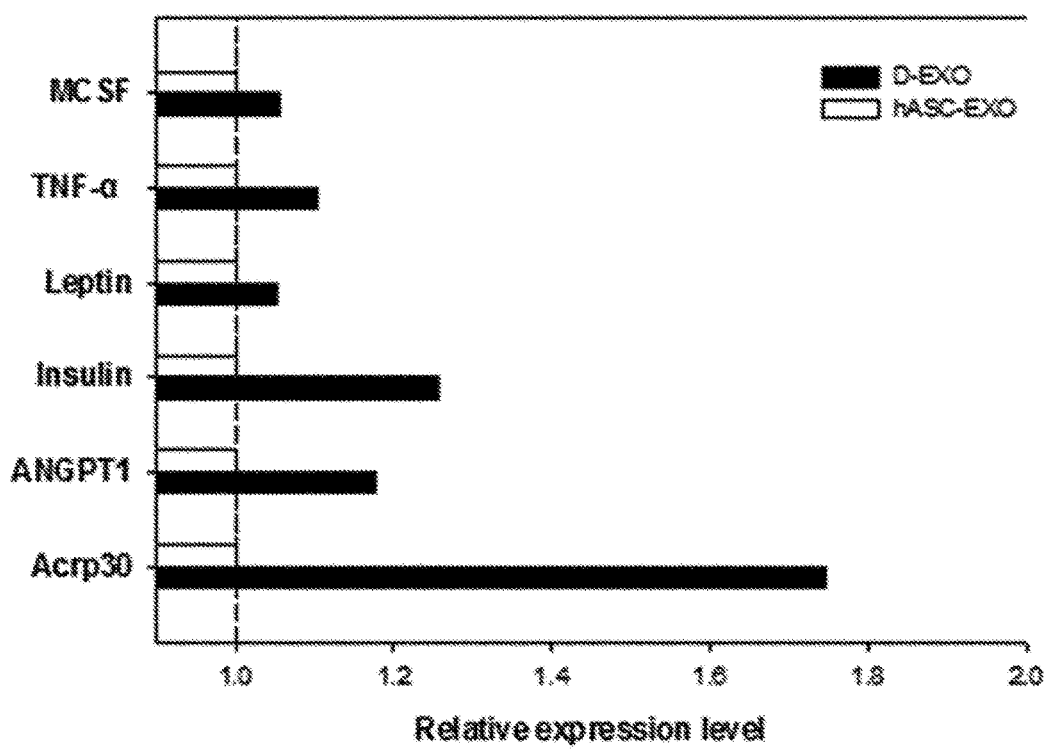

[FIG. 6]
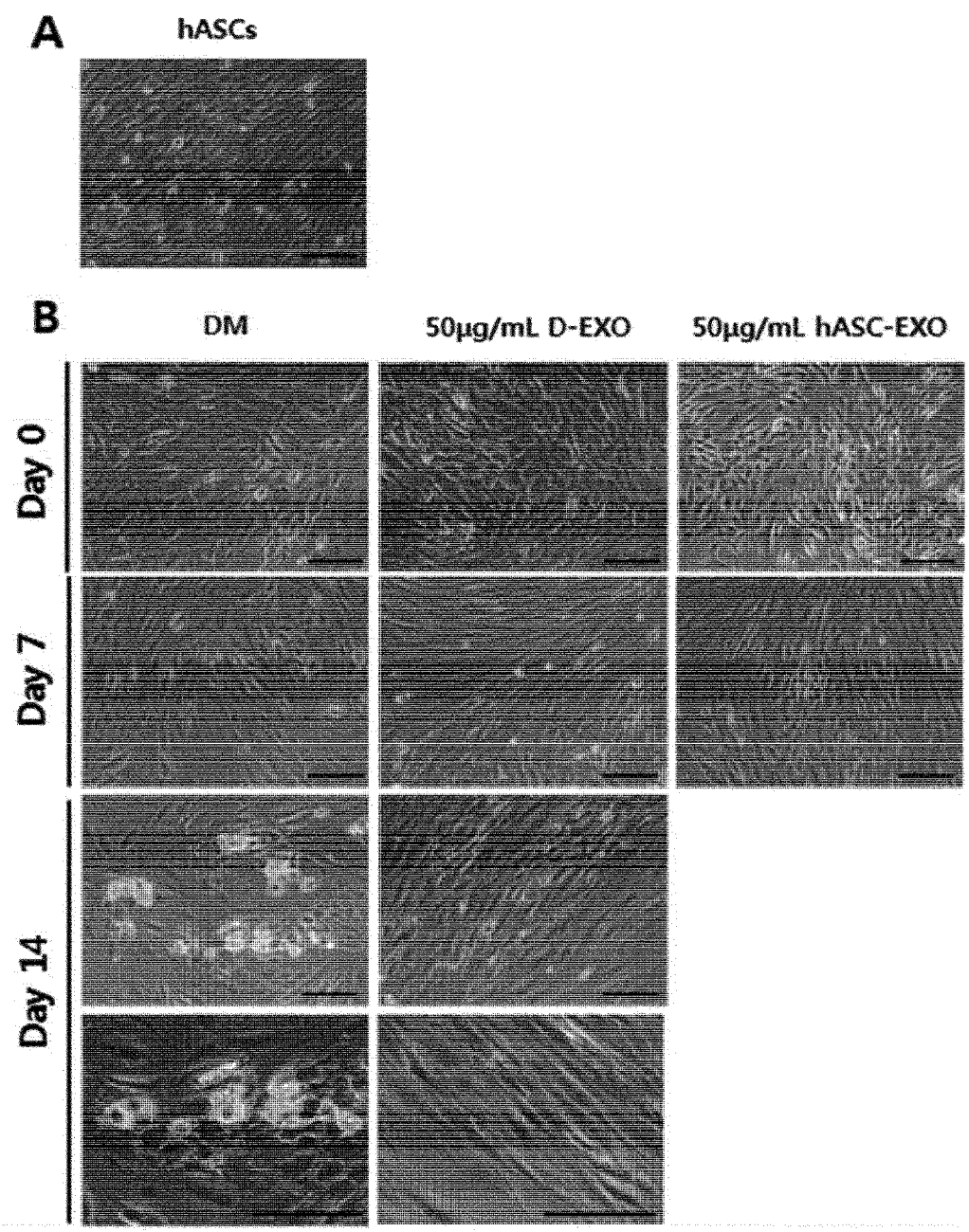

[FIG. 7]
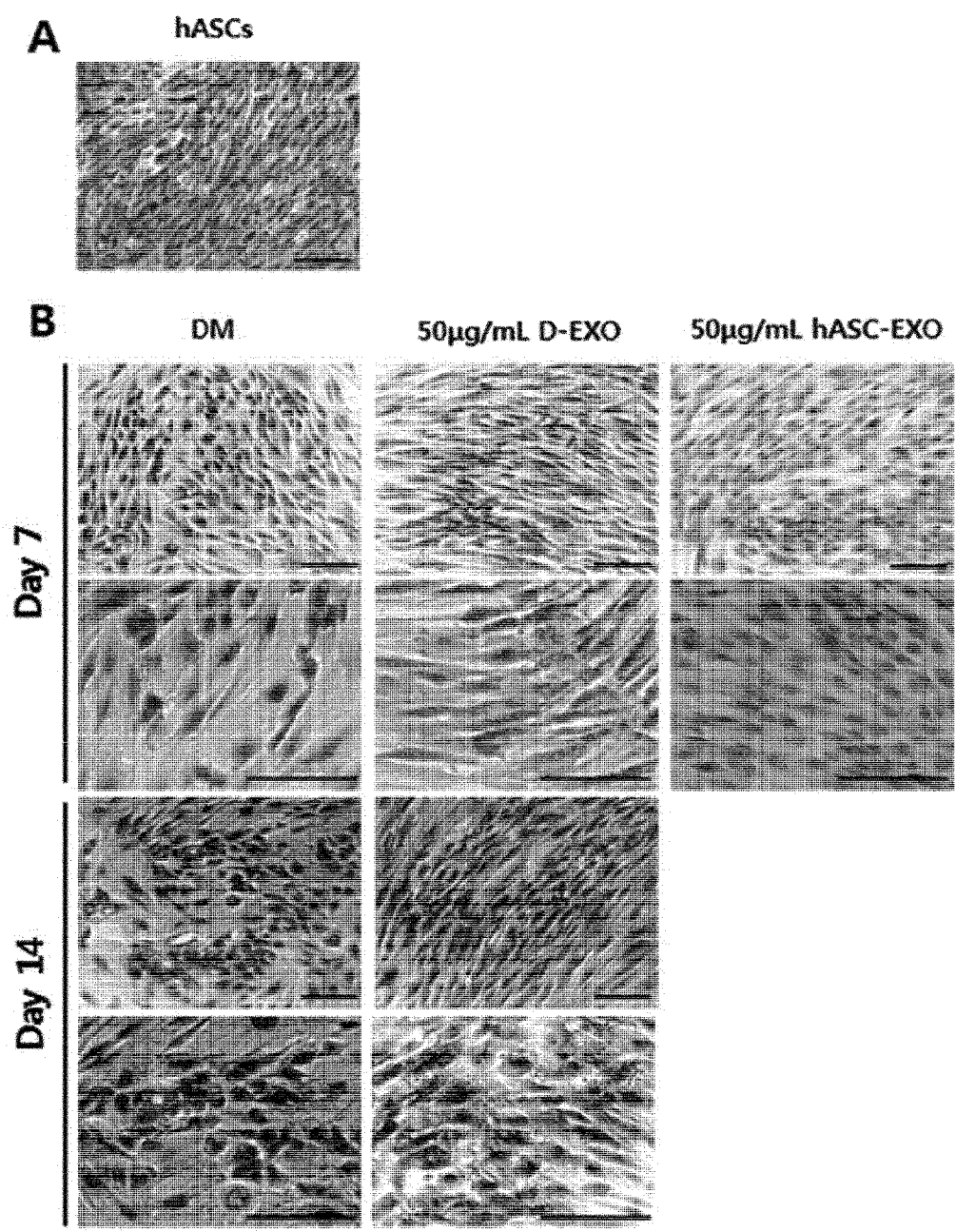

[FIG. 8]
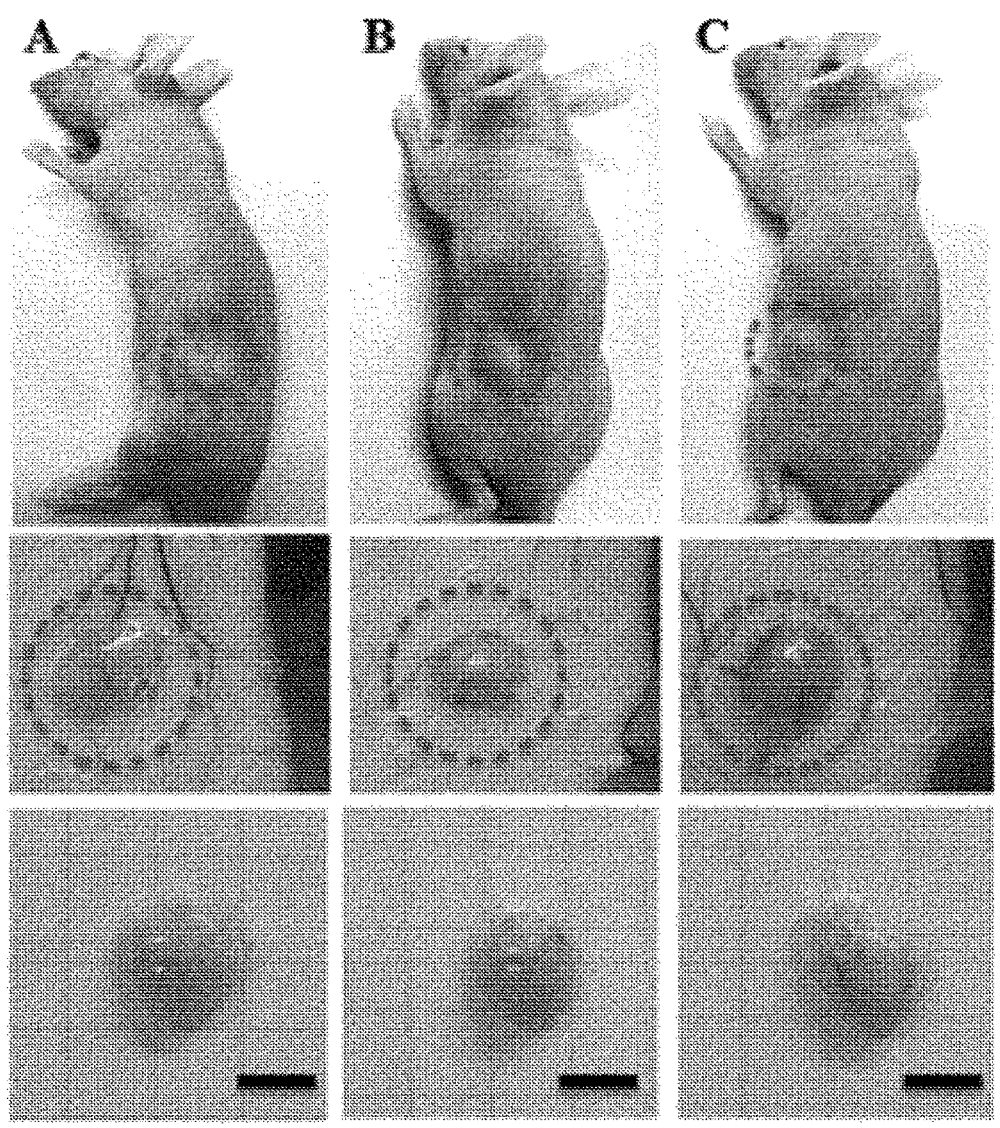

[FIG. 9]
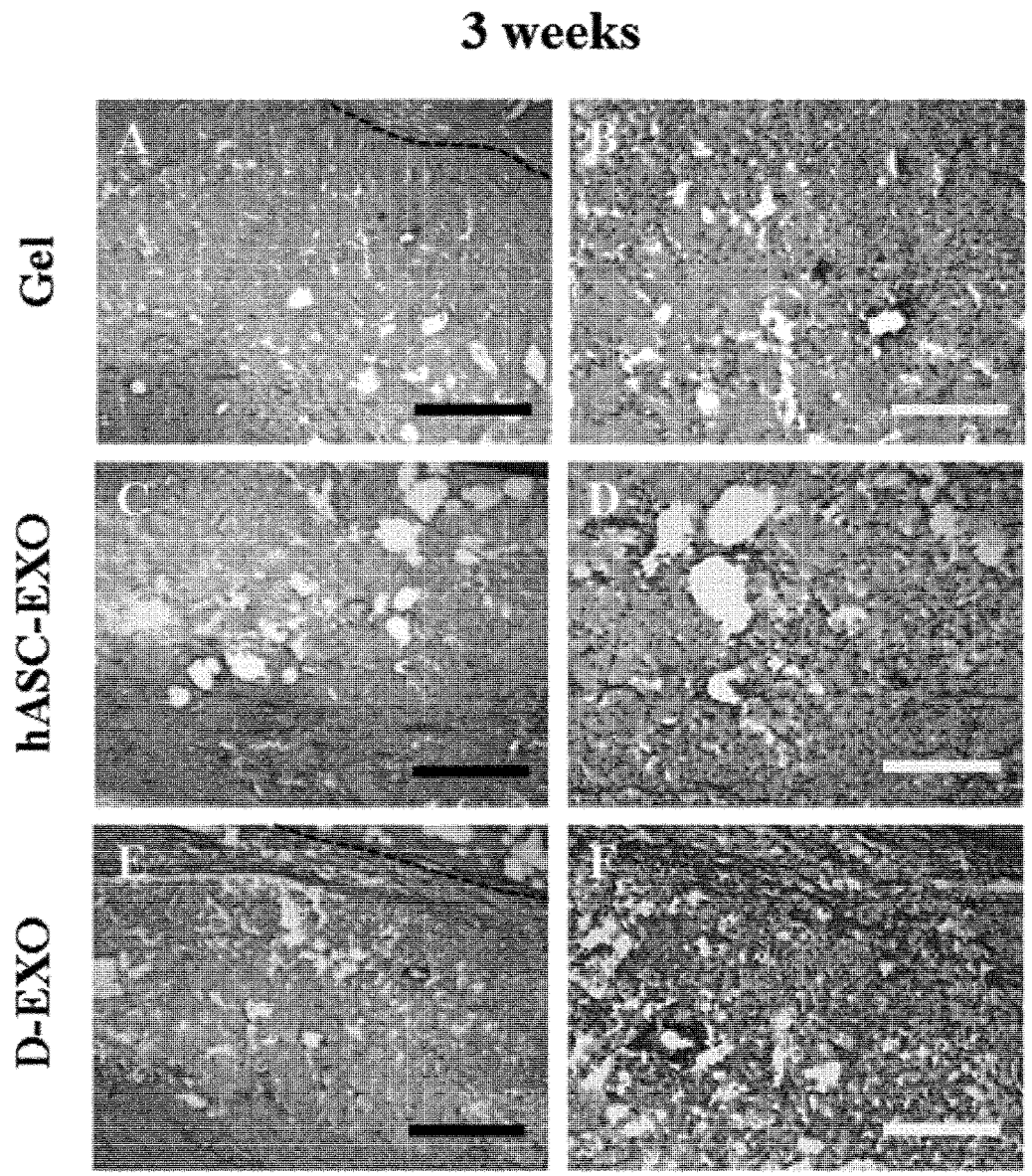

[FIG. 10]
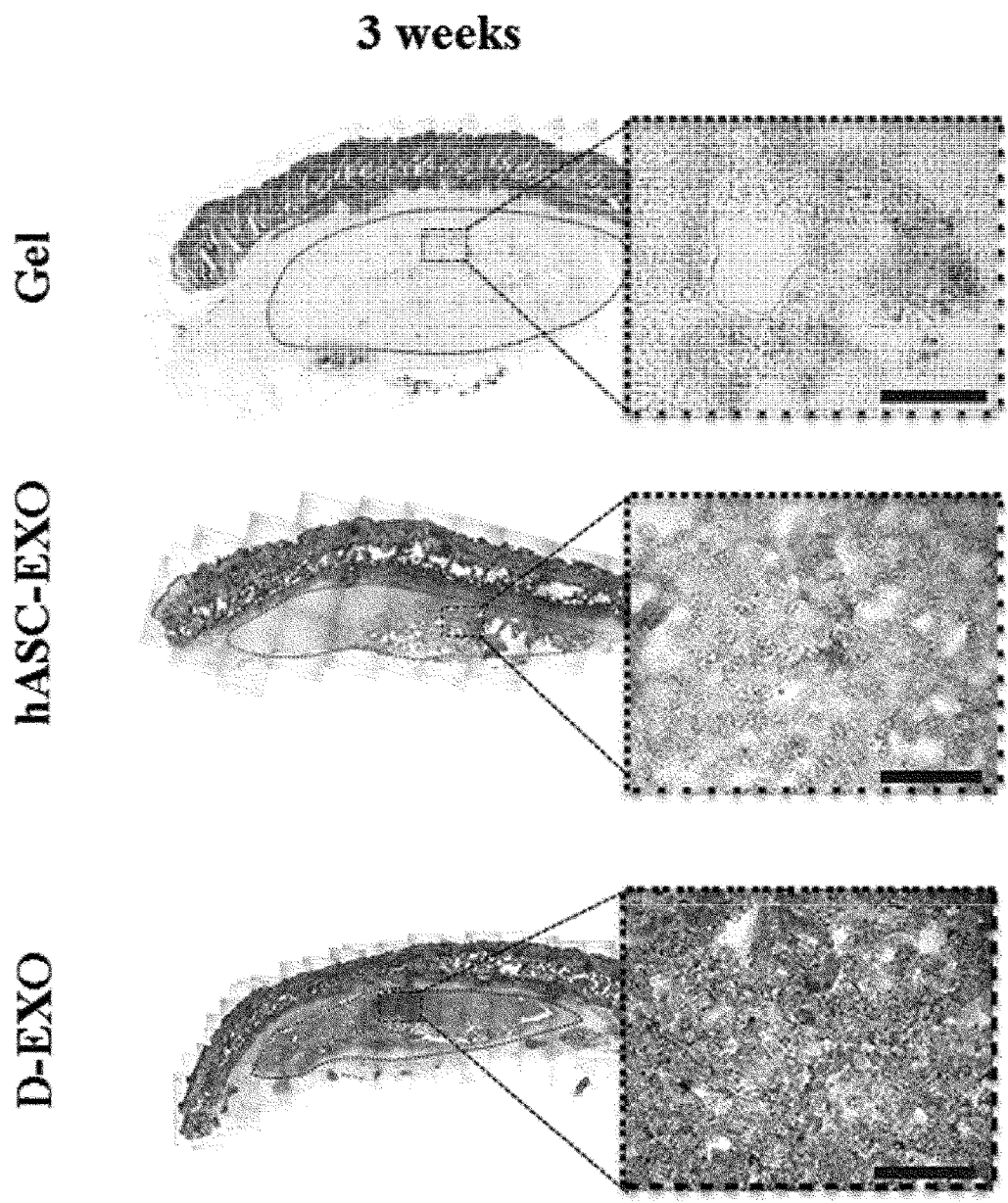

[FIG. 12]
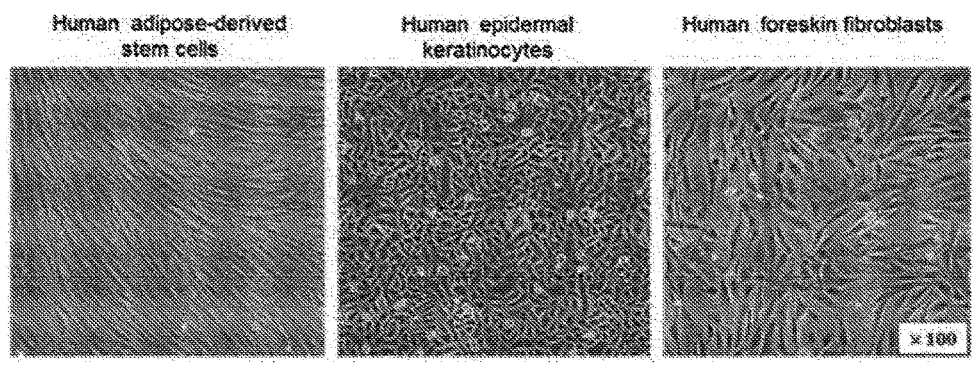

[FIG. 13A]
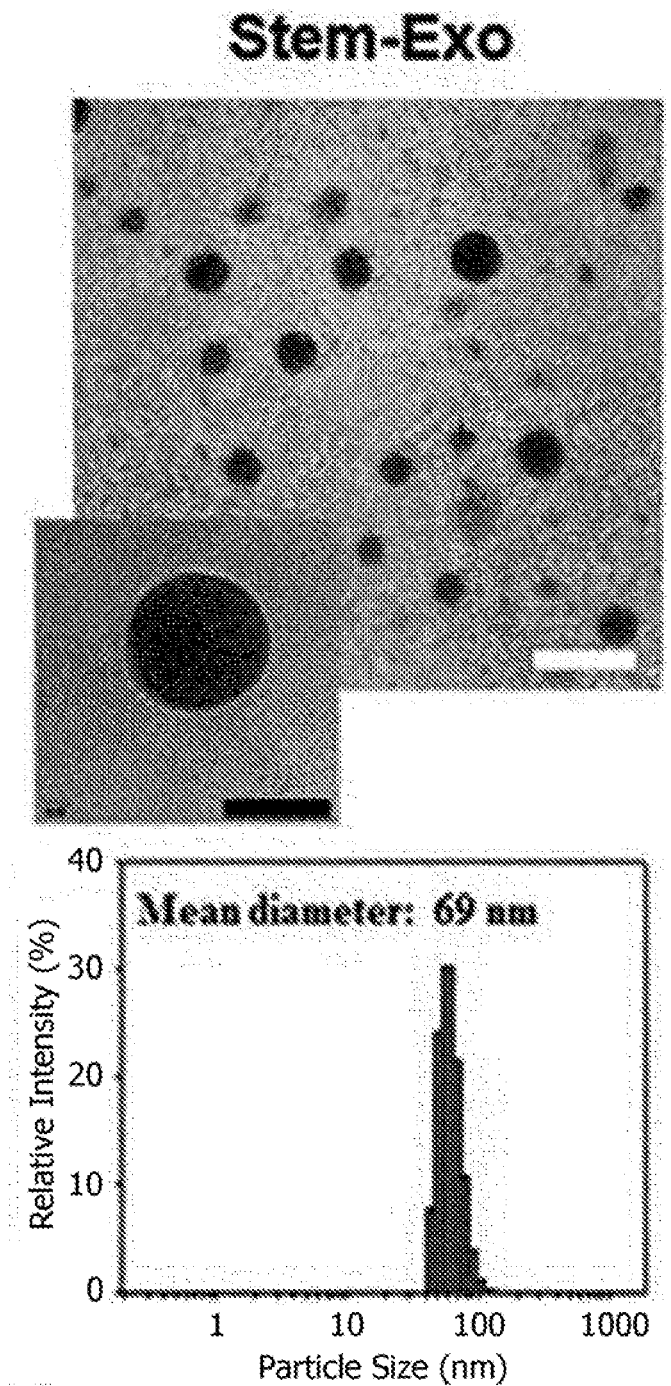

[FIG. 13B]
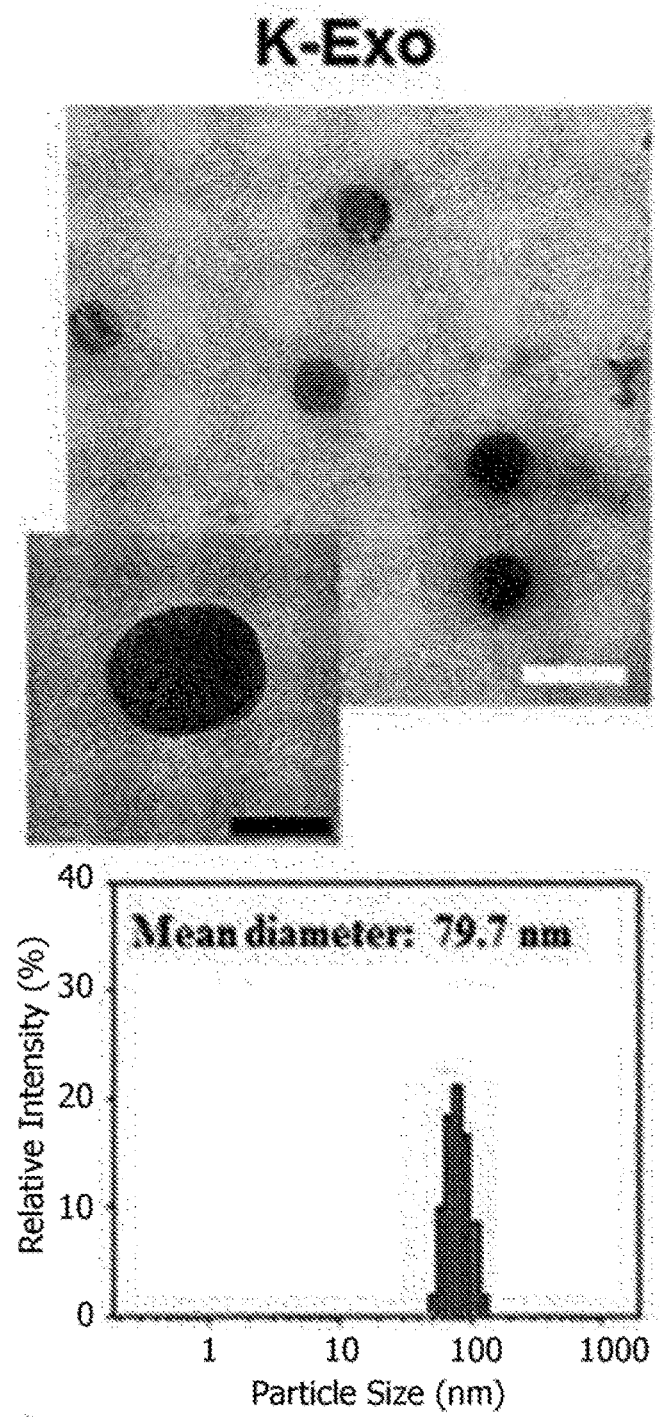

[FIG. 13C]
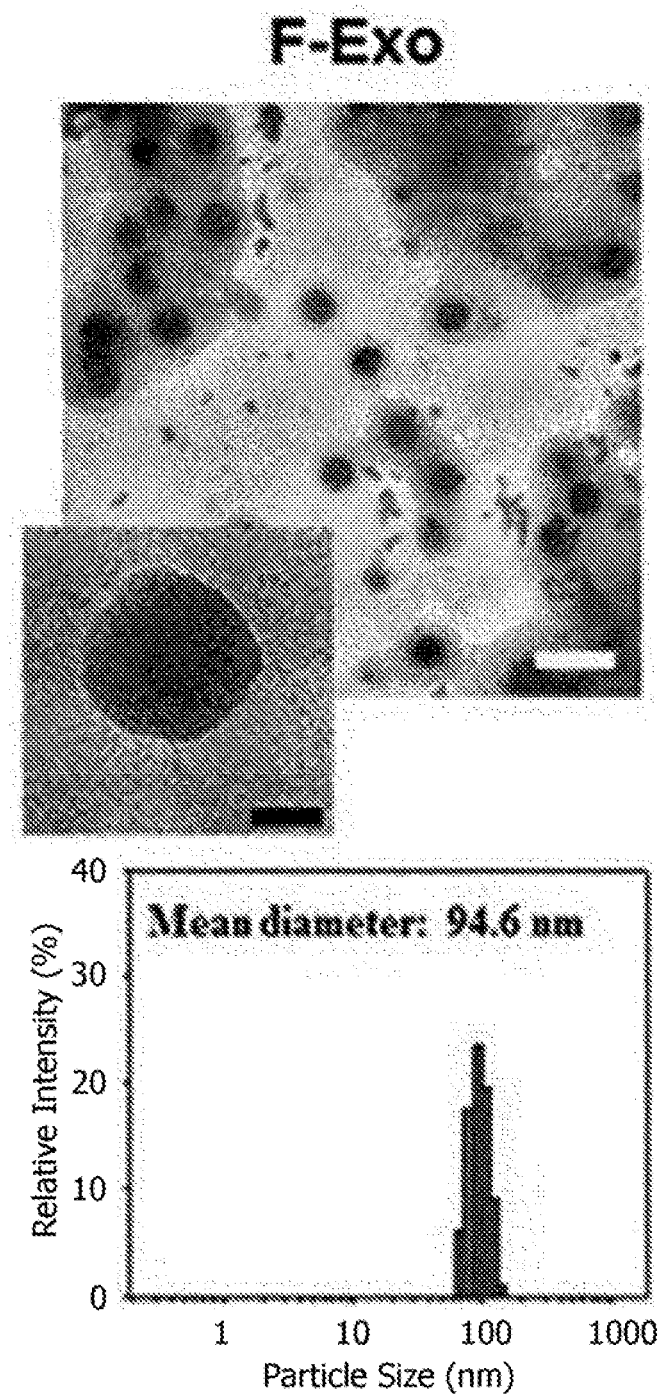

[FIG. 14A]
[FIG. 14B]

COSMETIC COMPOSITION CONTAINING EXOSOMES EXTRACTED FROM STEM CELL FOR SKIN WHITENING, ANTIWRINKLE OR REGENERATION

CROSS REFERENCE TO RELATED APPLICATION

This application is a continuation application of International application number PCT/KR2015/012013, filed Nov. 9, 2015, which claims priority to and the benefit of Korean Patent Applications No. 10-2014-0154410, 10-2015-0002660, 10-2015-0134689, and 10-2015-0137635, filed on Nov. 7, 2014, Jan. 8, 2015, Sep. 23, 2015, and September 30, the entire contents of which are incorporated herein by reference.

TECHNICAL FIELD

The present invention relates to a composition for inducing stem cells to differentiate into adipocytes and/or regenerating adipose tissues using a stem cell-derived exosome containing a differentiation-inducing substance for the adipocytes. Further, the present invention relates to a cosmetic composition for skin whitening, wrinkle improvement or skin regeneration containing an exosome derived from stem cells.

BACKGROUND

As a therapeutic method for regenerating adipose tissues, there is a method for using a therapeutic agent comprising stem cells, which are cultured with a matrix having an adipose tissue three-dimensionally cultured in a hydrogel. After three-dimensionally culturing the tissue in a hydrogel, a growth factor and an extracellular matrix may be secreted from the stem cells. However, to use the therapeutic agent as an injectable preparation type, it was inconvenient to remove the hydrogel in the form of a film from a culture container and to treat the tissue with a lyase. To overcome such inconvenience, a therapeutic method for regenerating tissues by autologous fat grafting or directly transplanting stem cells has been developed.

In the case of autologous fat grafting, the method uses parts of the body of a subject under operation. Therefore, the method incurs no issue of tissue or immune rejection and no observed immune response. However, the adipose tissue is highly oxygen-dependent and interacts with neighboring cells while having many blood vessels around. The grafted fat hardly exhibits a blood vessel-forming ability, and thus has disadvantages. For example, a cell apoptosis or cell necrosis may be induced due to hypoxia, and the subject may need to receive several procedures as the rate of engraftment is not high.

Formerly, stem cells have frequently been used to restore damaged tissues that have been limited by surgery or drug therapy. For example, biopolymers such as hyaluronic acid and collagen are used for stem cell transplantation. Since stem cells can differentiate into various cells including adipocytes, these stem cells have a wide range of applications. However, since the survival rate and the engraftment rate are low once they are placed into the body, the efficiency is reduced. Also, there is a risk that undifferentiated stem cells can form tumors.

Currently, a method for differentiating stem cells into adipocytes for tissue regeneration generally includes treating differentiation-inducing materials such as insulin, dexamethasone, isobutylmethylxanthine, etc. on stem cells and culturing them for a long time. However, the above-mentioned stem cell differentiation-inducing materials are expensive and are not effective for differentiation only by a single component. Thus, they have disadvantages. For example, they must be treated by mixing various substances, and the efficiency of cell differentiation is low. This is problematic.

On the other hand, conventionally, attempts have been made to use a culture solution obtained by culturing stem cells as a cosmetic. In general, a culture medium containing an appropriate amount of antibiotics and serum is used for culturing stem cells. Most of the stem cell culture solutions developed as cosmetic compositions use a normal culture medium, and a cosmetic composition including a liposome in which a culture solution of stem cells is encapsulated in a liposome. Further, a cosmetic composition using a culture medium prepared without the ingredients that are not permitted as raw materials for cosmetics and a cosmetic composition containing a serum-free culture medium, and the like have been developed.

The culture media are substances containing proteins, amino acids, hormones and growth factors for cell proliferation. The media have been prepared in a very sophisticated manner and supplied. However, since the cell culture media, antibiotics and serum have risks that are not proven as safe, they should be used only for research purposes and their use for the human body is prohibited. The components included in the culture media, such as choline chloride, hypoxanthine-sodium salt, thymidine, putrescine dihydrochloride, ferric nitrate, L-glutamine and the like, are not permitted as raw materials for cosmetics. Thus, the use of such culture media is not suitable for a cosmetic composition. As such, the culture media contain various proteins, cytokines, growth factors and the like secreted by stem cells. In contrast, they also contain components such as waste products secreted as cells grow, antibiotics added to prevent contamination, or animal-derived serum, etc. Thus, they are highly likely to pose various risks when used on the skin.

The components of the stem cell culture solutions to be used for cosmetics are limited. Also, during the process of encapsulating into the liposomes, the deterioration and contamination of the components of the culture solutions, and an additional treatment process of encapsulating with liposomes are required. Thus, the technique of encapsulating the stem cell culture solutions with liposomes including lipids to increase the skin absorption rate of the culture solutions is also limited in the use for a cosmetic.

To complement the disadvantages of these stem cell culture solutions, techniques for using stem cell-derived exosomes have been developed. Stem cells are usually cultured in a medium containing antibiotics and serum. Bio-nanoparticles secreted from various cells present in multicellular organisms including humans can be classified into exosomes and micro-vesicles depending on their size and difference in secretion mechanism. It is known that exosomes, which are vesicles of membrane structures secreted from various types of cells, play a variety of roles. For example the roles include transferring membrane components, proteins, RNA, etc. by binding to other cells and tissues. Most of secretomes including the exosomes are obtained from a cell culture supernatant. Thus, under a stem cell-derived exosome isolation method currently used, it is difficult to completely purify the exosomes due to interference by proteins in the medium or serum in the step of isolating the secretomes including the exosomes.

Accordingly, the present inventors have isolated exosomes from stem cells and discovered that the stem cell-derived exosomes have the effects of stem cell differentiation, adipose tissue regeneration, whitening, wrinkle improvement and skin regeneration.

SUMMARY

One embodiment of the present invention provides a composition for inducing differentiation into adipocytes or regenerating adipose tissues. The composition may include, as an active ingredient, an exo some derived from proliferating stem cells, or an exosome derived from stem cells differentiating into adipocytes.

As used herein, the "stem cells differentiating into adipocytes" refer to stem cells which are differentiating into adipocytes, for example, from adipose tissue-derived stem cells (ASCs). An example of adipose tissue-derived stem cells is shown in FIG. 1. From this, the exosomes containing genetic information, proteins and growth factors may be isolated.

Specifically, when stem cells differentiate into adipocytes, their shapes are clearly changed, and the exosomes are isolated at this time. Therefore, it is different from isolating exosomes from undifferentiated stem cells.

Exosomes refer to cell-derived messenger vesicles containing cell-specific components that play a role in cell-to-cell communication by merging with a recipient cell. In an embodiment, exosomes are of endocytic origin and are vesicles, involved in cell communication, secreted from a cell that contain cell-specific components, such as lipids, genetic material, and proteins. For example, exosomes refer to vesicles, typically 40-100 nm in size, secreted by various types of cells and are known to carry out various roles such as transferring membrane components, proteins, and RNA by binding to other cells and tissues. Exosomal markers include tetraspanins (CD9, CD63 and CD81) and multivesicular body (MVB) synthesis proteins (Alix and TSG101).

The exosome may be prepared by an exosome isolation method known in the art or by the following steps, for example, 1) culturing stem cells in a culture medium, and then sub-culturing in a serum-free and non-antibiotic medium; 2) recovering the cell culture supernatant; 3) centrifuging the recovered cell culture supernatant; and 4) separating and purifying the exosomes, but is not limited thereto.

The stem cells differentiating into adipocytes may be bone marrow stem cells, cord blood stem cells or adipose-derived stem cells, and may be human-, animal- or plant-derived stem cells, but are not limited thereto.

The exosome may be used on stem cells at a concentration of 1 to 150 μg per 1 mL of the composition for inducing differentiation into adipocytes or regenerating adipose tissues, specifically at a concentration of 5 to 150 μg, more specifically at a concentration of 10 to 150 μg, even more specifically at a concentration of 20 to 130 μg, and further more specifically at a concentration of 20 to 100 μg, but is not limited thereto.

As used herein, the term "inducing differentiation into adipocytes" refers to the induction of stem cells to differentiate into adipocytes.

The composition may include, as an active ingredient, an exosome derived from stem cells differentiating into adipocytes according to one embodiment of the present invention. The composition may differentiate stem cells into adipocytes. Therefore, the composition may be used as a composition for inducing differentiation into adipocytes.

As used herein, the term "regenerating adipose tissues" refers to the regeneration of adipose tissues by recovering damaged adipose tissues or inducing the production of deficient adipose tissues.

Further, the composition may regenerate adipose tissues. Therefore, the composition may be used as a composition for regenerating adipose tissues.

The composition for inducing differentiation into adipocytes or regenerating adipose tissues according to another embodiment of the present invention may be used as a pharmaceutical composition. Specifically, the pharmaceutical composition may be contained in an amount of 0.001 to 10 parts by weight based on 100 parts by weight of the total composition.

The pharmaceutical composition according to the above embodiment may be various oral or parenteral formulations. The formulations may be prepared using a diluting agent or an excipient, such as commonly-used fillers, weighting agents, bonding agents, wetting agents, disintegrating agents, surfactants and the like. The solid formulations for oral administration include tablets, pills, powders, granules, capsules and the like. Such solid formulations may be prepared by mixing at least one compound with at least one excipient, for example, starch, calcium carbonate, sucrose or lactose, gelatin and the like. In addition to simple excipients, lubricants, such as magnesium stearate, talc and the like may also be used. Liquid formulations for oral administration include suspension, liquid for internal use, emulsion, syrup and the like. In addition to commonly used simple diluents such as water and liquid paraffin, the liquid formulations may also include various excipients, for example, wetting agents, sweetening agents, flavoring agents, preservatives and the like. The formulations for parenteral administration include sterile aqueous solutions, non-aqueous solvents, suspensions, emulsions, lyophilization formulations and suppositories.

As for the pharmaceutical composition according to the above embodiment, vegetable oil, such as propylene glycol, polyethylene glycol, and olive oil, and an injectable ester, such as ethyl oleate and the like may be used as the non-aqueous solvents and suspending agents. Witepsol, macrogol, tween 61, cacao butter, laurinum, glycerol gelatin and the like may be used as a suppository base.

The dosage forms of the pharmaceutical composition according to the above embodiment may be in the form pharmaceutically acceptable thereof, or it may be used alone or in suitable combination with other pharmaceutically active compounds. The salt of the exosome compound is not particularly limited as long as it is pharmaceutically acceptable. The salt includes, for example, the salts of hydrochloric acid, sulfuric acid, nitric acid, phosphoric acid, hydrofluoric acid, hydrobromic acid, formic acid, acetic acid, tartaric acid, lactic acid, citric acid, fumaric acid, malic acid, succinic acid, methanesulfonic acid, benzenesulfonic acid, toluenesulfonic acid, naphthalene sulfonic acid and the like.

The pharmaceutical composition according to the above embodiment may be parenterally or orally administered depending on the purpose, and may be administered once or multiple times daily as needed such that the amount administered is 0.1 to 500 mg, 1 to 100 mg per kg. The effective dosage for a specific patient varies depending on the patient's body weight, age, gender, health conditions, diet, the period of administration, the mode of administration, excretion rate, the severity of the disease and the like.

According to a conventional method, the pharmaceutical compositions according to the above embodiments may be used by formulating into any form suitable for a pharmaceutical formulation including oral compositions such as powders, granules, tablets, capsules, suspensions, emulsions, syrups, aerosols and the like, external preparations such as ointments, creams and the like, suppositories and sterilized injectable solutions.

The pharmaceutical compositions according to the above embodiments may be administered to mammals such as rats, mice, livestock, humans and the like using various routes such as parenteral, oral and the like, and although all routes of administration can be expected, it may preferably be administered via oral, rectal or intravenous, intramuscular, subcutaneous, intrauterine, or intracerebroventricular injection.

The pharmaceutical composition for inducing differentiation into adipocytes or regenerating adipose tissues may further include differentiation-inducing materials such as insulin, dexamethasone, dehydroepiandrosterone (DHEA), histamine and isobutylmethylxanthine, etc. in order to differentiate stem cells into adipocytes, but is not limited thereto.

Another embodiment of the present invention provides a cosmetic composition for inducing differentiation into adipocytes or regenerating adipose tissues and may include, as an active ingredient, an exosome derived from stem cells differentiating into adipocytes.

The cosmetic composition may promote the regeneration of adipose tissues by inducing differentiation into adipocytes.

The exosome may be contained in the cosmetic composition at a concentration of 1 to 150 μg per 1 mL of the cosmetic composition, specifically at a concentration of 5 to 150 μg, more specifically at a concentration of 10 to 150 μg, even more specifically at a concentration of 20 to 130 μg, and further more specifically at a concentration of 20 to 100 μg, but is not limited thereto.

The cosmetic composition according to the above embodiment may contain adjuvants commonly used in cosmetic or dermatological science such as fatty substances, organic solvents, solubilizing agents, thickening agents, gelling agents, softening agents, antioxidants, suspending agents, stabilizing agents, foaming agents, flavoring agents, surfactants, water, ionic or non-ionic emulsifiers, fillers, sequestering agents, chelating agents, preservatives, vitamins, blockers, wetting agents, essential oils, dyes, pigments, hydrophilic or lipophilic active agents, lipid vesicles or any other ingredient commonly used in cosmetics. Such adjuvants are introduced in the amounts commonly used in the cosmetic or dermatological fields.

The external form of the cosmetic composition according to the above embodiment contains a cosmetically or dermatologically acceptable medium or base. The cosmetic composition may be in any form suitable for topical application. For example, the cosmetic composition may be provided in the form of solutions, gels, solids, a paste, anhydrous products, emulsions obtained by dispersing oil phase in aqueous phase, suspensions, microemulsions, microcapsules, or ionic (liposomes) and non-ionic vesicle dispersants, and these compositions may be prepared according to a conventional method in the art.

The cosmetic composition according to the above embodiment is preferably applied in the form of being absorbed into the skin using a microneedle, etc., but is not limited thereto.

The cosmetic composition for inducing differentiation into adipocytes or regenerating adipose tissues may include, as an active ingredient, an exosome derived from stem cells differentiating into adipocytes. The cosmetic composition may further include differentiation-inducing materials such as insulin, dexamethasone, dehydroepiandrosterone (DHEA), histamine and isobutylmethylxanthine, etc. in order to differentiate stem cells into adipocytes, but is not limited thereto.

Still another embodiment of the present invention provides a medium composition for stem cell differentiation which contains an exosome derived from stem cells differentiating into adipocytes and induces the stem cells to differentiate into adipocytes.

The exosome may be contained in the medium composition for stem cell differentiation at a concentration of 1 to 150 μg per 1 mL of the medium composition for stem cell differentiation, specifically at a concentration of 5 to 150 μg, more specifically at a concentration of 10 to 150 μg, even more specifically at a concentration of 20 to 130 μg, and further more specifically at a centration of 20 to 100 μg, but is not limited thereto.

The medium composition for stem cell differentiation may further include a stem cell culture medium, but is not limited thereto.

The medium composition for stem cell differentiation may further include differentiation-inducing materials such as insulin, dexamethasone, dehydroepiandrosterone (DHEA), histamine and isobutylmethylxanthine, etc. to differentiate stem cells into adipocytes, but is not limited thereto.

Further another embodiment of the present invention provides an injectable preparation comprising a composition for inducing differentiation into adipocytes or regenerating adipose tissues. The injectable preparation may include, as an active ingredient, an exosome derived from stem cells differentiating into adipocytes; and a hydrogel.

The exosome may be contained in the injectable preparation at a concentration of 1 to 150 μg per 1 mL, specifically at a concentration of 5 to 150 μg, more specifically at a concentration of 10 to 150 μg, even more specifically at a concentration of 20 to 130 μg, and further more specifically at a concentration of 20 to 100 μg, but is not limited thereto.

The hydrogel may be at least one hydrogel such as gelatin, alginate, chitosan, fibrin, elastin, hyaluronic acid, collagen, methyl cellulose, or collagen and methylcellulose hydrogel, but is not limited thereto.

The injectable preparation may be an injectable preparation for inducing differentiation into adipocytes or regenerating adipose tissues, but is not limited thereto. That is, when the injectable preparation of the present invention is administered to an animal via an injection, the effects of inducing differentiation into adipocytes or regenerating adipose tissues may be exhibited.

In one embodiment of the present invention, the hydrogel was prepared by adding methylcellulose powder to a collagen solution. Specifically, the methylcellulose powder was added to a collagen solution dissolved in 0.02 N acetic acid at a concentration of 3 mg/mL such that the final concentration of methylcellulose was 6% by weight. Then, the mixture was stirred at 4° C. for 1 hour to prepare collagen and methyl cellulose hydrogel.

In one embodiment of the present invention, the injectable preparation was prepared by carrying the exosomes, which are derived from stem cells differentiating into adipocytes, in the collagen and methylcellulose hydrogel. Specifically, the exosomes derived from stem cells differentiating into adipocytes were carried in the hydrogel to a final concentration of 50 μg/mL, and then dispersed in the hydrogel by pipetting.

The injectable preparation according to the above embodiment may be administered to mammals such as rats, mice, livestock, humans and the like via oral, rectal or intravenous, intramuscular, subcutaneous, intrauterine or intracerebroventricular injection.

In one embodiment of the present invention, the exosomes derived from the stem cells differentiating into adipocytes according to the present invention, as compared with the exosomes derived from proliferating stem cells, show an excellent expression rate of bioactive factors affecting the differentiation into adipocytes (FIGS. 4 and 5).

In another embodiment of the present invention, the exosome derived from the stem cells differentiating into adipocytes according to the present invention, and the exosome derived from the proliferating stem cells, as a control group, were added in an experiment for differentiating stem cells into adipocytes. In these instances, it was confirmed that, when the exosomes according to the present invention were used, the adipocytes differentiated at a level similar to that of the stem cells cultured in the differentiation medium on day 7, and accordingly, oil was produced. However, in the case of the stem cells treated with the exosomes derived from the proliferating stem cells, it was confirmed that these stem cells only proliferated without being differentiated into adipocytes (FIGS. 6 and 7).

In still another embodiment of the present invention, the injectable preparation in which the exosomes derived from the stem cells differentiating into adipocytes according to the present invention were carried in the collagen/methylcellulose hydrogel showed an excellent effect on the regeneration of adipose tissues compared to the injectable preparation carried with the exosomes derived from the proliferating stem cells (FIGS. 9 and 10).

The composition for stem cell differentiation and adipose tissue regeneration according to the above embodiment includes the exosomes containing genetic information, proteins and growth factors of adipocytes related to the differentiation into adipocytes. Thus, the composition can be effectively used for the differentiation of stem cells as it is not necessary to add complex and various growth factors for differentiation. The stem cells differentiate into adipocytes by the exosomes derived from the stem cells differentiating into adipocytes of the present invention, thereby exerting an advantageous effect on the regeneration of adipose tissues when applied in vivo. The exosome derived from the stem cells differentiating into adipocytes of the present invention is a cell-derived material and thus is biocompatible, minimizing the side effects of the existing cell therapy agents. Further, the exosome itself can act as a carrier, which enables easy application of the components carried therein to the human body. Thus, the exosome can be applied as a stem cell differentiation inducer, an injectable preparation for tissue regeneration, a filler for cosmetic purposes, a formulation for tissue engineering and the like.

Another embodiment of the present invention provides a cosmetic composition containing, as an active ingredient, an exosome derived from stem cells, and more specifically, a cosmetic composition for skin whitening, wrinkle improvement or skin regeneration containing, an active ingredient, an exosome derived from stem cells.

The exosome derived from the stem cell in a serum-free, and non-antibiotic medium contains extracellular matrix derivatives as well as collagen and growth factors effective for skin regeneration and thus can be effectively applied for skin improvement.

In the above embodiment, the term "stem cells" refers to stem cells that proliferate. From this, it is possible to isolate exosomes containing the genetic information of the stem cells, proteins and growth factors.

The stem cells may be bone marrow stem cells, cord blood stem cells or adipose-derived stem cells, and may be human-, animal- or plant-derived stem cells, but are not limited thereto.

As used herein, the term "human adipose-derived stem cells" refer to stems cells derived from human adipocytes. From this, it is possible to isolate exosomes containing the genetic information, proteins and growth factors of the stem cells.

The method of isolating exosomes may be carried out by a method known in the art, but is not limited thereto. In one embodiment of the present invention, the exosomes were isolated during the process of subculturing human adipose-derived stem cells. Specifically, the human adipose tissue-derived stem cells (passages 3 to 7) were cultured in a normal culture medium (Dulbecco Modified Eagle Medium, DMEM containing 10% fetal bovine serum, 1% penicillin/streptomycin). Then, at 24 hours before isolating the exosomes, the cell culture media were replaced with DMEM medium, which is a serum-free and non-antibiotic medium without phenol red, and then maintained for 24 hours. After 24 hours, the cell culture supernatant was recovered. The recovered cell culture supernatant was centrifuged at 300×g for 10 minutes to remove the cells, and then centrifuged at 2,000×g for 30 minutes to remove the cell secretion. Thereafter, the cells were concentrated by centrifugation at 5,000×g for 60 minutes using a centrifuge tube equipped with a filter having a molecular weight of 3,000. The supernatant obtained after the concentration was mixed with an exosome isolation reagent at a ratio of 1:0.5 and stored at 4° C. for one day. An exosome precipitate was obtained by centrifugation at 10,000×g for 60 minutes, then filtered through a 0.22 μm filter and washed with phosphate-buffered saline (PBS). The washed exosome precipitate was centrifuged at 10,000×g for 60 minutes and resuspended in PBS (FIG. 1). After recovering the supernatant, the normal culture medium was added to the stem cells and cultured. This procedure was repeated up to passages 7 of the stem cells. The cosmetic composition was prepared using the exosomes isolated during the process of proliferating the stem cells up to passages 7.

The exosome may be contained at a concentration of 1 to 150 μg per 1 mL of the cosmetic composition in the cosmetic composition for skin whitening, wrinkle improvement or regeneration, specifically at a concentration of 5 to 150 μg, more specifically at a concentration of 10 to 150 μg, even more specifically at a concentration of 20 to 130 μg, and further more specifically at a centration of 20 to 100 μg, but is not limited thereto.

In one embodiment of the present invention, the exosomes derived from human adipose-derived stem cells were used at a concentration of 10, 30 or 50 μg/mL. Further, an excellent wound healing of human foreskin fibroblasts (FIG. 18), an excellent collagen synthesis rate (FIG. 19) and a decrease in melanin synthesis (FIG. 20) were confirmed.

The exosome may be contained in the cosmetic composition in the form of a liposome encapsulating the exosome by encapsulating the exosome into the liposome, but is not limited thereto. In some embodiments, the exosome may be in any form as long as it is suitable for use as a cosmetic composition. It is also possible to use the exosome itself without being encapsulated into a liposome.

When the exosome is used in the form of liposome encapsulation, the exosome may be contained in an amount of 0.1 to 10.0% by weight, more specifically in an amount of 0.1 to 1.0% by weight based on the total weight of the liposome, but is not limited thereto.

The liposome encapsulating the exosome may be contained in an amount of 0.001 to 10.0% by weight, specifically in an amount of 0.001 to 1.0% by weight, more specifically in an amount of 0.01 to 1.0% by weight, and even more specifically in an amount of 0.01 to 0.1% by weight based on the total weight of the entire cosmetic composition, but is not limited thereto.

In one embodiment of the present invention, 3% by weight of lecithin was dispersed in an aqueous phase containing 0.01% by weight of the exosomes derived from the stem cells at room temperature (e.g., 15° C.), and then a reverse micelle emulsion (water/low temperature process carbon dioxide) was formed using supercritical carbon dioxide. Then, the reaction was terminated, and the supercritical carbon dioxide was vaporized under reduced pressure to remove the supercritical carbon dioxide phase, thereby obtaining a low-temperature process liposome suspension in which the exosomes are encapsulated. The cosmetic composition was prepared such that the thus-prepared liposome encapsulating the exosomes was contained in an amount of 5% by weight based on the total weight of the entire cosmetic composition.

In conventional technology, a culture solution obtained during the culturing of human adipose-derived stem cells was used. However, the aforesaid embodiment is different therefrom in that the exosome in the form of a nano-vesicle present in the culture solution is isolated and purified to be used as a cosmetic ingredient, without using the culture solution as it is. When the stem cell exosomes are isolated and purified, the regeneration-related proteins, collagen derivatives and various growth factors contained in the exosomes can be effectively used in such a mariner that they eliminate interference from medium components. Thus, the problems caused by the medium components including antibiotics and serum can be solved.

The exosome according to the above embodiment contains the genetic information, protein and growth factors of the stem cells, and the exosome itself can serve as a carrier. The exosome composed of lipids of about 50 to 150 nm in size is biocompatible because it is a cell-derived material, and shows an excellent cell absorption rate. Therefore, it has advantages in that no additional processes of encapsulating the culture solution into the liposome are necessary as in the conventional technology, and that it can be easily applied to the skin.

Further, the cosmetic composition containing the exosomes derived from the stem cells according to the above embodiment may be used as a formulation for improving the appearance of scars. Since the stem cell derived-exosomes contain proteins and growth factors that induce cell proliferation and differentiation, and skin regeneration, they can be applied to old wounds and acne scars to reduce scarring or the appearance thereof. Therefore, when used as a formulation for improving scar tissue, it can be applied in the form of sprays, a gel-type ointments and patches containing the exosome derived from stem cells, etc.

In addition, still further another embodiment of the present invention provides a pharmaceutical composition containing, as an active ingredient, an exosome derived from stem cells, more specifically, a pharmaceutical composition for skin regeneration containing, as an active ingredient, an exosome derived from stem cells. Accordingly, the cosmetic composition for skin regeneration containing, as an active ingredient, an exosome derived from stem cells according to one embodiment of the present invention may be used as a pharmaceutical composition.

The stem cells may be bone marrow stem cells, cord blood stem cells or adipose-derived stem cells, and may be human-, animal- or plant-derived stem cells. For example, these stem cells may be human adipose-derived stem cells, but are not limited thereto.

In one embodiment of the present invention, when the size of the exosome derived from proliferating human adipose-derived stem cells (Stem-EXO) was examined, the size was about 69 nm, confirming that it is smaller than the exosome derived from human epidermal keratinocytes (K-EXO) or the exosome derived from human foreskin fibroblasts (F-EXO) (FIG. 13).

In another embodiment of the present invention, when the bioactive factors involved in wrinkle improvement, whitening and skin regeneration present in Stem-EXO, K-EXO and F-EXO were compared and analyzed, it was confirmed that the monocyte chemoattractant protein-1, -3 (MCP-1, -3), chemokine ligand 5 (CCL-5) and collagenase inhibitor (the tissue inhibitor of metalloproteinase-1 (TIMP-1)) related to the mechanisms associated with promoting collagen synthesis and inhibiting the degradation thereof, interleukin-6, -8 (IL-6, -8) associated with whitening, hepatocyte growth factor (HGF), plasminogen activator inhibitor-1 (PAI-1), angiogenin and angiopoietin-1 associated with skin regeneration and angiogenesis were over-expressed in Stem-EXO compared to K-EXO and/or F-EXO (FIGS. 15, 16 and 17).

In still another embodiment of the present invention, the wound healing effect of the human foreskin fibroblasts in Stem-Exo was examined. As a result, when Stem-EXO was used at a concentration of 10, 30 and 50 μg/mL, it showed an excellent effect on the migration of foreskin fibroblasts compared to K-EXO or F-EXO, thereby showing an excellent effect on would healing (FIG. 18).

In further another embodiment of the present invention, the wrinkle improvement effect of Stem-EXO was confirmed. As a result, the collagen synthesis was increased as the concentration at which the Stem-EXO was used increased. Specifically, Stem-EXO showed a remarkably excellent collagen synthesis rate compared to K-EXO or F-EXO at 50 μg/ml, thereby confirming an excellent effect on the wrinkle improvement (FIG. 19).

In still another embodiment of the present invention, the inhibitory effect of Stem-EXO on melanin formation was examined. As a result, when Stem-EXO was used on mouse melanoma at a concentration of 10, 30 and 50 μg/mL, it was confirmed that the melanin synthesis was decreased, thereby confirming a remarkably excellent whitening effect (FIG. 20).

The exosomes according to embodiments of the present invention show an excellent expression rate of bioactive factors influencing the differentiation into adipocytes and have the effect of differentiating stem cells into adipocytes. Accordingly, the present invention can be applied as stem cell differentiation inducing agents, injectable preparations for tissue regeneration, fillers for cosmetic purposes, preparations for tissue engineering, etc. Further, the exosomes according to embodiments of the present invention are exosomes which are secreted during the proliferation of stem cells and contain genes, proteins, growth factors and the like associated with cell proliferation, differentiation and regeneration of stem cells, and thus can induce skin regeneration without other additives such as cell activators or growth factors. Furthermore, the exosomes are purified components which do not include antibiotics, serums or harmful factors of a culture solution, and thus, the problems associated with culture cosmetics can be overcome. Further, the exosomes are cell-derived lipid carriers, thereby showing excellent cell infiltration and being highly effective in delivering effective factors. Accordingly, the present invention can be applied to functional cosmetic compositions having skin whitening, wrinkle improvement and skin regeneration functions, and preparations for improving the appearance of scars for cosmetic purposes, etc.

BRIEF DESCRIPTION OF THE DRAWINGS

FIG. 1 is a schematic diagram of the exosomes derived from stem cells differentiating into adipocytes and the application thereof FIG. 2 is a schematic diagram of the method for isolating exosomes from stem cells differentiating into adipocytes.

FIG. 3A to 3C shows diagrams illustrating the characteristics of the exosomes derived from stem cells differentiating into adipocytes; A: structure and shape of the exosomes (transmission electron microscope), B: size of the exosome (nanoparticle analyzer, dynamic light scattering), C: exosome membrane surface marker (Western Blot).

FIG. 4A to 4C shows diagrams illustrating lipid-related bioactive factors in the exosomes through a microarray; A: exosomes derived from proliferating stem cells (hASC-EXO), B: exosomes derived from stem cells differentiating into adipocytes (D-EXO), C: adipokine array map.

FIG. 5 shows a diagram illustrating the expression rate of factors affecting the differentiation into adipocytes; exosomes derived from proliferating stem cells (hASC-EXO) and exosomes derived from stem cells differentiating into adipocytes (D-EXO).

FIG. 6 shows the result of inducing differentiation of human adipose-derived stem cells into adipocytes; A: human adipose-derived stem cells (hASCs), B: positive control group (DM), exosomes derived from stem cells differentiating into adipocytes (D-EXO) and exosomes derived from proliferating stem cells (hASC-EXO).

FIG. 7 shows the result of Oil red O staining of stem cells induced to differentiate into adipocytes; A: human adipose-derived stem cells (hASCs), B: positive control group (DM), exosomes derived from stem cells differentiating into adipocytes (D-EXO) and exosomes derived from proliferating stem cells (hASC-EXO).

FIG. 8 shows the result of inducing the formation of adipose tissues for 3 weeks by carrying the exosomes in a hydrogel obtained by mixing collagen and methylcellulose and subcutaneously injecting the exosomes into nude mice models; A: collagen/methylcellulose hydrogel (Gel), B: hydrogel carrying the exosomes derived from proliferating stem cells (hASC-EXO), C: hydrogel carrying the exosomes derived from stem cells differentiating into adipocytes (D-EXO).

FIG. 9 shows the result of hematoxylin-eosin staining of the gels subcutaneously injected into nude mice models. One gel does not carry the exosome (Gel), and the other gels carry the exosomes derived from proliferating stem cells (hASC-EXO) and the exosomes derived from stem cells differentiating into adipocytes (D-EXO), respectively. A, C, E: 40× magnification; B, D, F: 100× magnification.

FIG. 10 shows the result of Oil red O staining of the gels subcutaneously injected into nude mice models. One gel does not carry the exosome (Gel), and the other gels carry the exosomes derived from proliferating stem cells (hASC-EXO) and the exosomes derived from stem cells differentiating into adipocytes (D-EXO), respectively.

FIG. 12 shows images of human adipose-derived stem cells, human epidermal keratinocytes, and human foreskin fibroblasts observed with a microscope.

FIG. 13A to 13C shows diagrams illustrating the characteristics of the exosomes derived from human adipose-derived stem cells (Stem-Exo). The exosomes derived from human keratinocytes (K-Exo) and from human foreskin fibroblasts (F-Exo) were used as control groups. The structure and shape of the exosomes (transmission electron microscope), and the size of the exosomes (nanoparticle analyzer, dynamic light scattering) were illustrated respectively; A: Stem-Exo (scale bars indicate 50 nm (black), 100 nm (white), respectively), B: K-Exo (scale bars indicate 50 nm (black), 100 nm (white), respectively) and C: F-Exo (scale bars indicate 50 nm (black) and 200 nm (white), respectively).

FIG. 14A to 14D shows diagrams showing a comparison of the expression levels of bioactive factors contained in the exosomes derived from human adipose-derived stem cells (Stem-EXO), the exosomes derived from human epidermal keratinocytes (K-EXO) and the exosomes derived from human fibroblasts (F-EXO) using a microarray; A: table of microarray, B: result of microarray, C and D: graph showing the relative expression levels of bioactive factors.

DETAILED DESCRIPTION OF THE PREFERRED EMBODIMENTS

Figure 11:
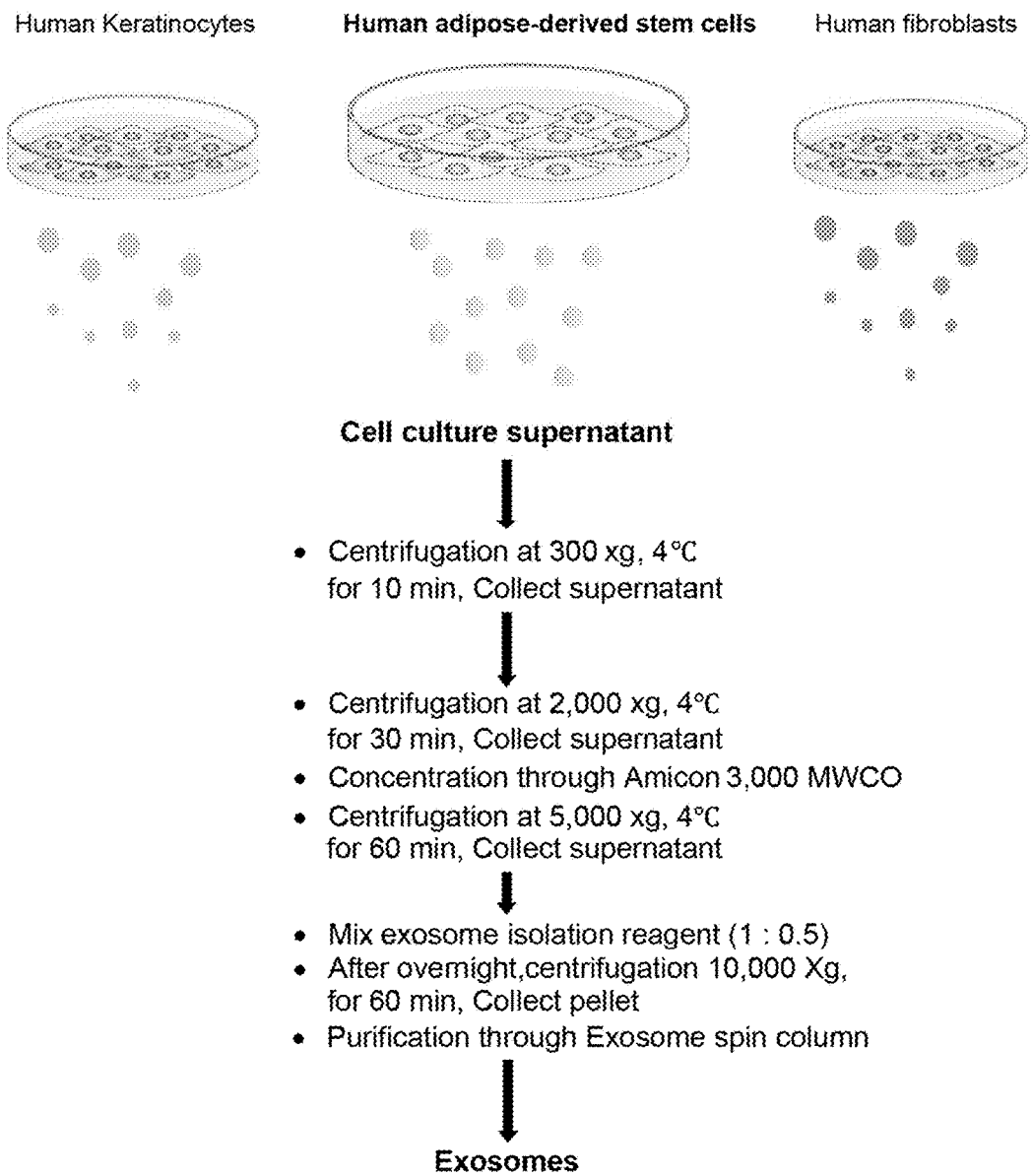
FIG. 11 is a schematic diagram of the method of isolating exosomes from proliferating human adipose-derived stem cells.

One aspect of the present invention is to provide a composition for inducing differentiation into adipocytes or regenerating adipose tissues. The composition may include, as an active ingredient, an exosome derived from stem cells differentiating into adipocytes, or an exosome derived from proliferating stem cells.

Another aspect of the present invention is to provide a cosmetic composition comprising a composition for inducing differentiation into adipocytes or regenerating adipose tissues. The cosmetic composition may include, as an active ingredient, an exosome derived from stem cells differentiating into adipocytes.

Still another aspect of the present invention is to provide a medium composition for inducing differentiation into adipocytes or regenerating adipose tissues. The medium composition may include, as an active ingredient, an exosome derived from stem cells differentiating into adipocytes.

Further another aspect of the present invention is to provide an injectable preparation comprising a composition for inducing differentiation into adipocytes or regenerating adipose tissues. The injectable preparation may include, as an active ingredient, an exosome derived from stem cells differentiating into adipocytes, and a hydrogel.

Still further another aspect of the present invention is to provide a cosmetic composition for skin whitening, wrinkle improvement or skin regeneration. The cosmetic composition may include, as an active ingredient, an exosome derived from proliferating stem cells.

Hereinafter, preferred embodiments are provided to help understanding of the present invention, but the embodiments are only for illustrative purposes. Further, it would be apparent to those skilled in the art that various modifications and alternative forms can be made within the scope and technical idea of the present invention, and that such modifications and alternative forms fall within the scope of the invention.

Some embodiments further relate to a method of inducing stem cells differentiating into adipocytes. For example, the method may include preparing exosomes derived from the stem cells differentiating into adipocytes and treating stem cells with the exosomes for a predetermined time period.

Some embodiments further relate to a method of inducing adipose tissue regeneration using exosomes. For example, the method may include preparing exosomes derived from the stem cells differentiating into adipocytes, placing the exosomes in a supporting material, and administering the supporting material to a subject, thereby regenerating adipose tissues. In some embodiments, the supporting material includes a hydrogel.

Some embodiments further relate to a method of producing a composition containing exosomes. For example, the method may include preparing exosomes derived from the stem cells differentiating into adipocytes and mixing the exosomes with any least one of stearic acid, cetyl alcohol, lanolin alcohol, liquid paraffin, Cyclomethicone, polyoxyethylene monoolein acid ester hexanediol, glycerin, triethylamine, or carbomer.

Some embodiments further relate to a method of improving migration of foreskin fibroblasts. For example, the method may include preparing exosomes derived from proliferating human adipose-derived stem cells and treating the foreskin fibroblasts with the exosomes, thereby improving the migration of the foreskin fibroblasts.

Some embodiments further relate to a method of improving collagen synthesis of foreskin fibroblasts. For example, the method may include preparing exosomes derived from proliferating human adipose-derived stem cells and treating the foreskin fibroblasts with the exosomes, thereby improving the collagen synthesis of the fore-skin fibroblasts.

EXAMPLE 1

Exosomes—Derived from Stem Cells Differentiating into Adipocytes

EXAMPLE 1-1

Isolation of Exosomes

In order to isolate the exosomes from stem cells differentiating into adipocytes, the differentiation into adipocytes was induced by culturing the stem cells in a differentiation medium.

The differentiation into adipocytes was confirmed as lipid droplets were formed in the cytoplasm while the stem cells became gradually uneven. The differentiating stem cell culture media were replaced with a serum-free medium and maintained for 48 hours, and the cell culture supernatant was recovered. The recovered cell culture supernatant was centrifuged at 300×g for 10 minutes to remove the cells, and then centrifuged at 2,000×g for 30 minutes to remove the cell secretion.

Thereafter, the cells were concentrated by centrifugation at 5,000×g for 60 minutes using a centrifuge tube (molecular weight cut off=3,000, amicon tube) equipped with a filter having a molecular weight of 3,000. The supernatant obtained after the concentration was mixed with an exosome isolation reagent at a ratio of 1:0.5 and stored at 4° C. for one day. Subsequently, the cells were centrifuged at 10,000×g for 60 minutes to obtain an exosome precipitate, then filtered through a filter (exosome spin column) having a molecular weight of 3,000, and washed with phosphate-buffered saline (PBS). The washed exosome precipitate was centrifuged at 10,000×g for 60 minutes and resuspended in PBS (FIG. 2).

EXAMPLE 1-2

Microscopic Analysis of Exosomes

The size and shape of the exosomes derived from Example 1-1 were confirmed using a transmission electron microscope and dynamic light scattering, and the surface protein of the exosomes was confirmed using Western Blot which detects a specific protein to the membrane surface of exosomes.

As a result, the exosomes isolated as shown in FIG. 3A were confirmed by a transmission electron microscope, and the size thereof was confirmed to be about 50.75 to 58.77 nm on average as shown in FIG. 3B. In addition, as shown in FIG. 3C, an exosome-specific marker expressed on the surface of the exosome membrane was confirmed through an antibody reaction.

EXAMPLE 1-3

Analysis of Proteins and Bioactive Factors Related to Adipocyte Differentiation in Exosomes A microarray was used to analyze the lipid-related bioactive factors present in the exosomes derived from stem cells differentiating into adipocytes and the exosomes derived from proliferating stem cells. The microarray was carried out through an antigen-antibody reaction, and the degree of fluorescence (Streptavidin-Cy3) expression was measured using a laser scanner (GenePix 4000B).

In addition, macrophage colony stimulating factor (MCSF), tumor necrosis factor-α (TNF-α), leptin, insulin, angiopoietinl (ANGPT1), and adipocyte complement-related protein of 30 kDa (Acrp30), all of which are bioactive factors influencing the differentiation into adipocytes among the factors expressed in the microarray analysis, were confirmed, and in this regard, the relative expression levels thereof in the exosomes derived from the stem cells differentiating into adipocytes and from proliferating stem cells were compared.

As a result, as shown in FIGS. 4A to 4C and Table 1, it was confirmed that there are different types of lipid-related bioactive factors present in the exosomes derived from the proliferating stem cells (hASC-EXO) and the exosomes derived from the stem cells differentiating into adipocytes (D-EXO), and it was also confirmed that there was a significant difference in the expression levels of bioactive factors affecting differentiation into adipocytes (FIG. 5).

TABLE 1

| hASC-EXO | | D-EXO |
|---|---|---|
| Adipsin | ACRP30* | OPG |
| CRP | ANGPT1* | PDGF-AB |
| Fas | ANGPTL4* | SDF-1 |
| IL-1 sRI | IL-1R4/ST2 | TECK |
| IL-6 | IL-10 | TGF-β* |
| MCP-1 | Insulin* | TIMP2 |
| MCP-3 | Leptin* | TNF-α* |
| PDGF-BB | MCSF* | XEDAR |

EXAMPLE 1-4

Induction of Adipocyte Differentiation Using Exosomes

In order to induce adipocyte differentiation of stem cells using the exosomes, medium compositions each containing the exosomes derived from proliferating stem cell culture medium and the exosomes derived from stem cells differentiating into adipocytes were used. The medium compositions were used by adding the exosomes to the stem cell culture medium at a concentration of 30, 50 and 100 μg/mL. After treating each medium composition on the cultured human adipose-derived stem cells (hASCs), the medium compositions were replaced once in every 3 days for 14 days.

The stem cells cultured in Dulbecco's Modified Eagle's Medium High Glucose medium (DMEM) containing 5% fetal bovine serum, 1 μM dexamethasone, 1 μg/mL insulin, 100 μM indomethacin, 0.5 mM 3-isobutyl-1-methylxanthine were used as a positive control group. The stem cells treated with the exosomes derived from proliferating stem cells were used as a positive control group. Then, the cell shape and whether the differentiation was carried out were analyzed with respect to the stem cells, in which the differentiation into adipocytes was induced, using a microscope and Oil-red O staining for 14 days.

As a result, when the exosomes derived from the stem cells differentiating into adipocytes (D-EXO) were used, the stem cells were differentiated into adipocytes at a level similar to that of the positive control (DM) on day 7 (FIG. 6), and accordingly, the production of oil was confirmed (FIG. 7). However, in the case of the stem cells treated with the exosomes derived from proliferating stem cells (hASC-EXO), it was confirmed that only proliferation was carried out without differentiation into adipocytes

EXAMPLE 1-5

Cosmetic Composition Comprising Exosomes Derived from Stem Cells Differentiating Into Adipocytes According to Example 1-1, a liposome encapsulating the exosomes—derived from stem cells differentiating into adipocytes was prepared. Specifically, 3% by weight of lecithin was dispersed in an aqueous phase containing 0.01% by weight of the exosomes derived from stem cells differentiating into adipocytes at room temperature (15° C.), and then a reverse micelle emulsion (water/low temperature process carbon dioxide) was prepared using supercritical carbon dioxide. Subsequently, the reaction was terminated, the supercritical carbon dioxide was vaporized under reduced pressure to remove the supercritical carbon dioxide phase, and a low temperature process liposome suspension, in which the exosomes derived from stem cells differentiating into adipocytes are encapsulated, was obtained. Here, the temperature of the reaction process was 4° C. or below.

The cosmetic composition was prepared by the composition shown in Table 2 below using the liposome encapsulating the exosomes.

TABLE 2

| Composition | Content (% by weight) |
|---|---|
| Stearic acid | 2 |
| Cetyl alcohol | 2 |
| Lanolin alcohol | 2 |
| Liquid paraffin | 7 |
| Cyclomethicone | 5 |
| Polyoxyethylene monooleic acid ester | 2 |
| Hexanediol | 2 |
| Glycerin | 3 |
| Triethylamine | 5 |
| Carbomer | 0.2 |
| Liposome encapsulating the exosomes according to Example 1-1 of the present invention | 0.01 |
| Purified water | remainder |

EXAMPLE 1-6

Induction of Adipose Tissue Regeneration Using Exosomes Derived from Stem Cells Differentiating into Adipocytes In order to confirm the effect on the adipose tissue regeneration when the exosomes derived from stem cells differentiating into adipocytes were injected into the body, the exosomes derived from the proliferating stem cells and the exosomes derived from stem cells differentiating into adipocytes were independently carried in a collagen/methylcellulose hydrogel.

Specifically, the hydrogel was prepared by adding methylcellulose powder to a collagen solution to form the collagen/methylcellulose hydrogel. That is, methylcellulose powder was added to a collagen solution dissolved in 0.02 N acetic acid at a concentration of 3 mg/mL such that the final concentration of methylcellulose became 6% by weight, and then the mixture was stirred at 4° C. for 1 hour to prepare the gel. In the thus-prepared collagen/methylcellulose hydrogel, the exosomes derived from the proliferating stem cells or the exosomes derived from stem cells differentiating into adipocytes were carried. Specifically, the exosomes were carried in the collagen/methylcellulose hydrogel to a final concentration of 50 μg/mL, and then dispersed in the hydrogel by pipetting. Further, the hydrogel containing the exosomes was subcutaneously injected into the nude mice and observed for 3 weeks. The hydrogel containing no exosome was used as a negative control group, and the hydrogel containing the exosomes derived from proliferating stem cells (hASC-EXO) was used as a positive control group (FIG. 8). Three weeks later, hematoxylin-eosin staining and oil red o staining were performed to confirm the regeneration of adipose tissues in the transplanted hydrogel.

As a result, a large amount of mouse cells was introduced into the gel containing the exosomes derived from the stem cells differentiating into adipocytes (D-EXO) (FIG. 9), and a large number of adipocytes in which oil was produced were observed (FIG. 10), as compared with the negative and positive control groups. From these results, it can be concluded that the exosomes derived from stem cells differentiating into adipocytes or the collagen/methylcellulose hydrogel carrying the exosomes were remarkably effective in inducing the regeneration of adipose tissues.

EXAMPLE 2

Exosomes Derived from Proliferating Stem Cells

EXAMPLE 2-1

Isolation of Exosomes from Proliferating Human Adipose-derived Stem Cells

The exosomes were isolated during the proliferation of human adipose-derived stem cells up to passages 7. That is, the exosomes were isolated from the proliferating human adipose-derived stem cells.

Specifically, the human adipose tissue-derived stem cells (passages 3 to 7) were cultured in a normal culture medium (Dulbecco Modified Eagle Medium (DMEM) containing 10% fetal bovine serum, 1% penicillin/streptomycin). Then, at 24 hours before isolating the exosomes, the cell culture media were replaced with DMEM medium, which is a serum-free and non-antibiotic medium without phenol red, and then maintained for 24 hours. After 24 hours, the cell culture supernatant was recovered. The recovered cell culture supernatant was centrifuged at 300×g for 10 minutes to remove the cells, and then centrifuged at 2,000×g for 30 minutes to remove the cell secretion. Thereafter, the cells were concentrated by centrifugation at 5,000×g for 60 minutes using a centrifuge tube equipped with a filter having a molecular weight of 3,000 (molecular weight cut off=3, 000, amicon tube). The supernatant obtained after the concentration was mixed with an exosome isolation reagent at a ratio of 1:0.5 and stored at 4° C. for one day. An exosome precipitate was obtained by centrifugation at 10,000×g for 60 minutes, then filtered through a 0.22 μm filter (exosome spin column) and washed with phosphate-buffered saline (PBS). The washed exosome precipitate was centrifuged at 10,000×g for 60 minutes and resuspended in PBS (FIG. 11). After recovering the supernatant, the normal culture medium was added to the stem cells and cultured. This procedure was repeated up to passages 7 of the stem cells. The exosomes isolated during the process of proliferating up to passages 7 were used in the following experiments. In order to compare with the efficacy of the exosomes from the human adipose-derived stem cells, the exosomes were isolated from human epidermal keratinocytes and human foreskin fibroblasts in the same manner by the above method (FIG. 12).

EXAMPLE 2-2

Microscopic Analysis of Exosomes

The sizes and shapes of the exosomes derived from human adipose-derived stem cells (Stem-Exo), the exosomes derived from human epidermal keratinocytes (K-Exo) and the exosomes derived from human foreskin fibroblasts (F-EXO) of Example 2-1 were confirmed by using a transmission electron microscope and dynamic light scattering.

As a result, the shape of each derived exosome was confirmed by a transmission electron microscope. In addition, the sizes of the exosomes derived from human adipose-derived stem cells, the exosomes derived from human epidermal keratinocytes, and the exosomes derived from human foreskin fibroblasts were about 69 nm, about 79.7 nm and about 94.6 nm, respectively, and the size of the exosomes (Stem-Exo) derived from the human adipose-derived stem cells was the smallest (FIGS. 13A to 13C).

EXAMPLE 2-3

Analysis of Proteins and Bioactive Factors Associated with Wrinkle Improvement, Whitening and Skin Regeneration in Exosomes A microarray analysis was performed to compare and analyze the bioactive factors associated with wrinkle improvement, whitening and skin regeneration present in the exosomes derived from human adipose-derived stem cells (Stem-Exo), exosomes derived from human epidermal keratinocytes (K-Exo) and exosomes derived from human foreskin fibroblasts (F-EXO). The microarray analysis was carried out through an antigen-antibody reaction, and the degree of fluorescence (Streptavidin-Cy3) expression was measured using a laser scanner (GenePix 4000B).

Figure 14C:
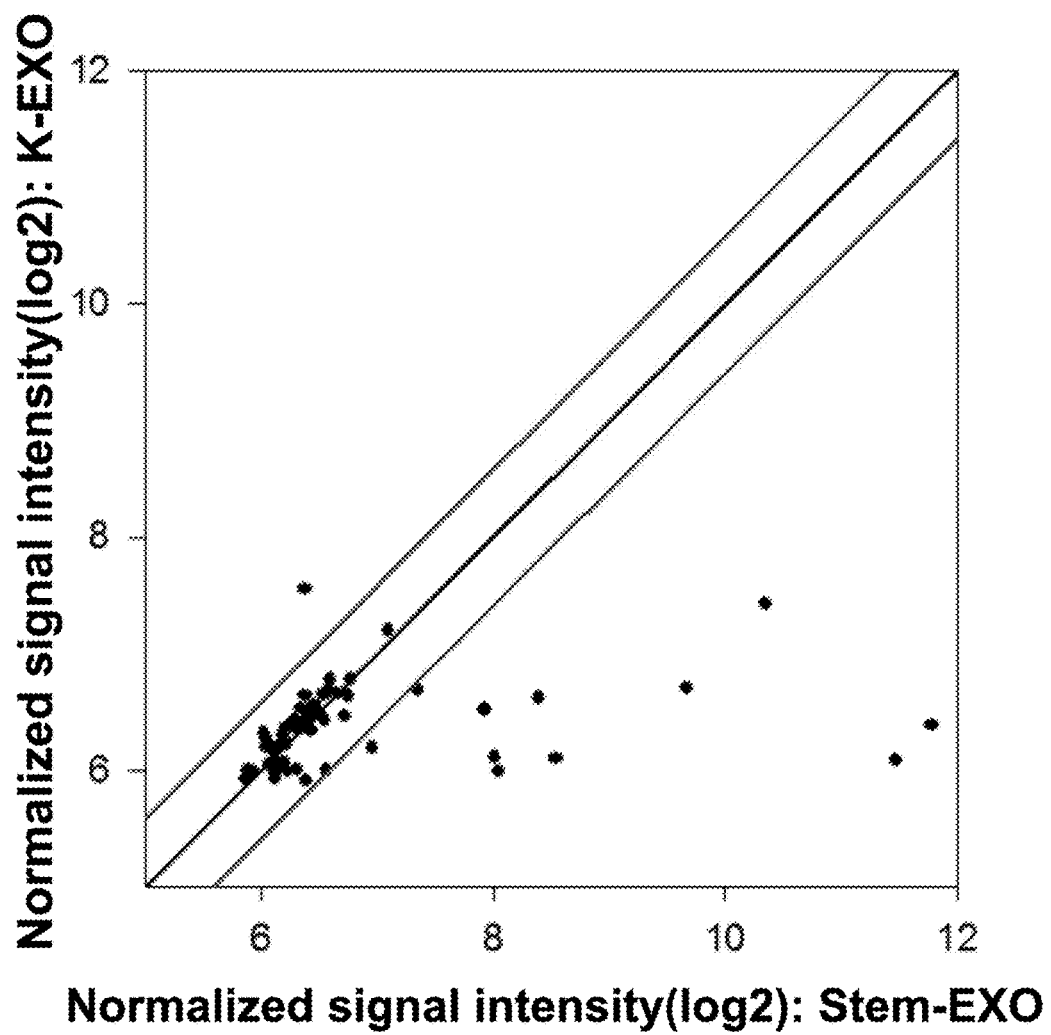
Figure 14D:
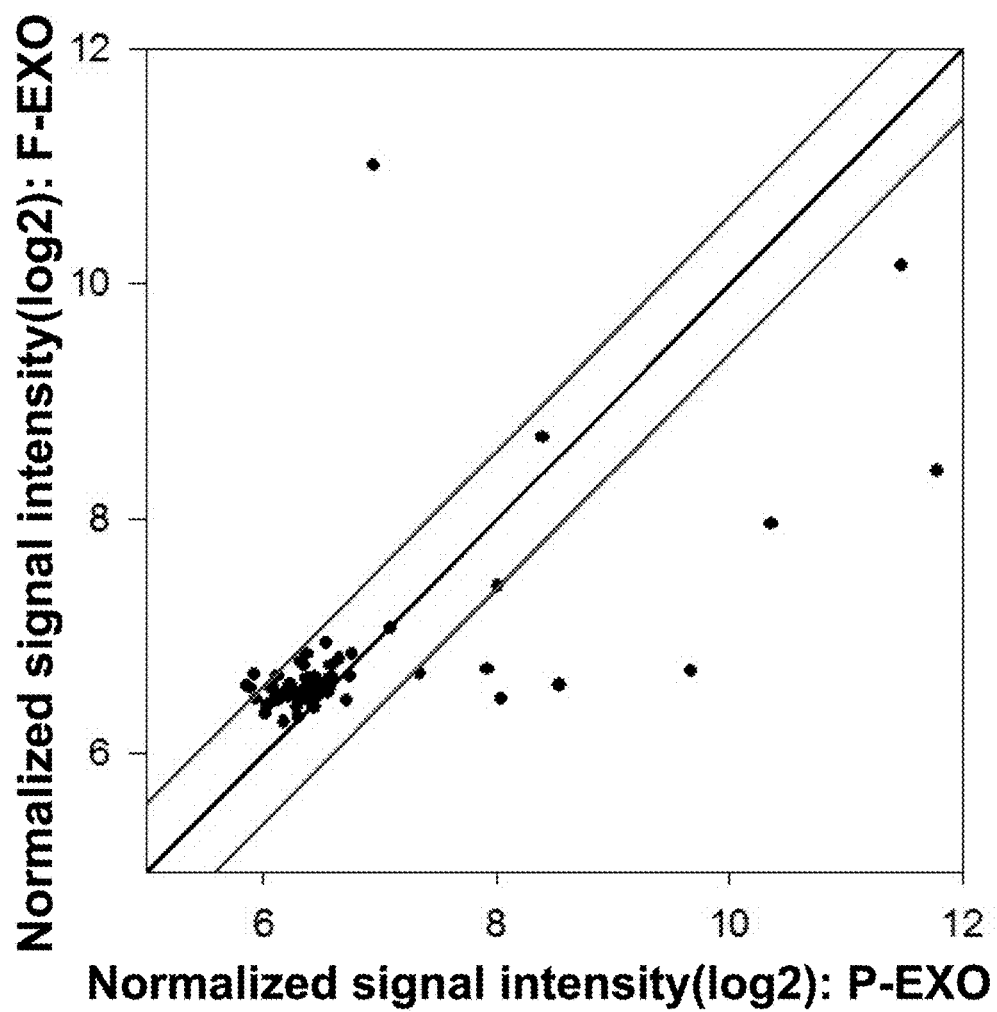
Figure 15A:
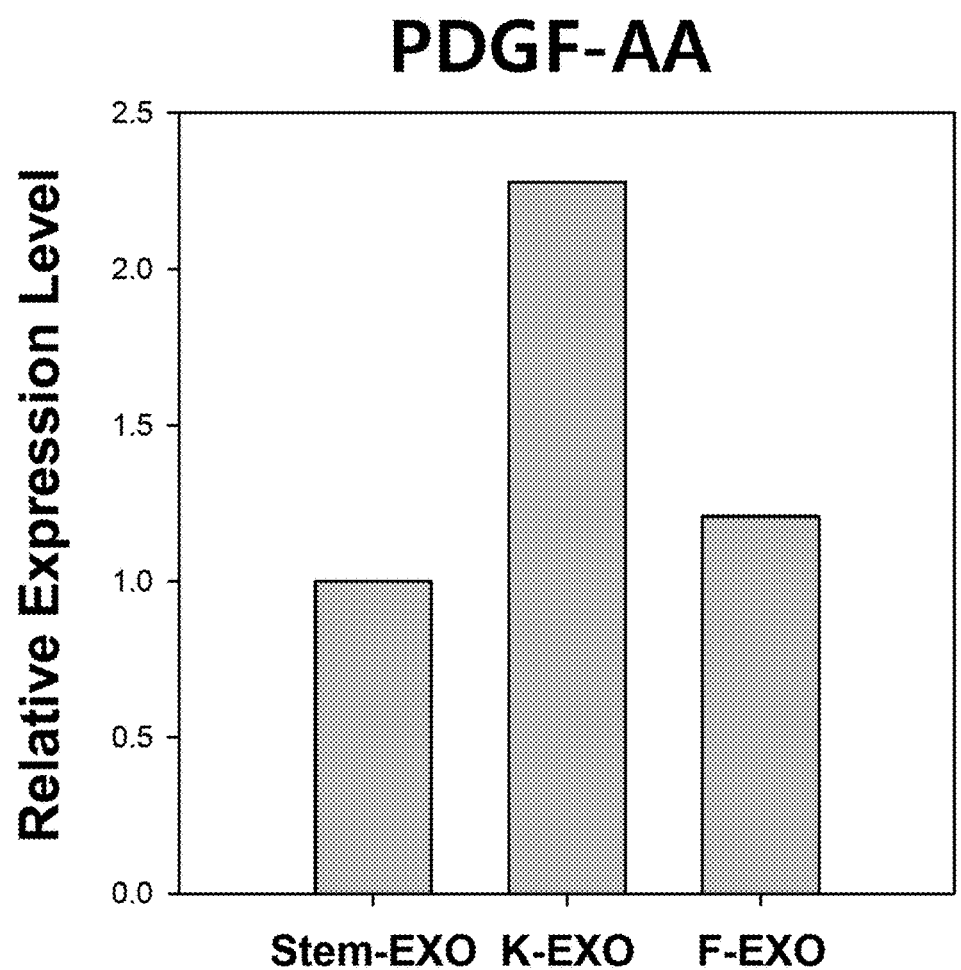
FIG. 15A to 15I shows graphs illustrating the expression level of bioactive factor (A: PDGF-AA, B: PDGF-AB, C: PDGF-BB, D: FGF-6, E: MCP-F: MCP-3, G: Eotaxin, H: CCL-5, I: TIMP-1) related to wrinkle improvement effect in the exosomes using a microarray; Stem-EXO: exosomes derived from proliferating human adipose-derived stem cells, K-EXO: exosomes derived from human epidermal keratinocytes, F-EXO: exosomes derived from human foreskin fibroblasts.
Figure 15B:
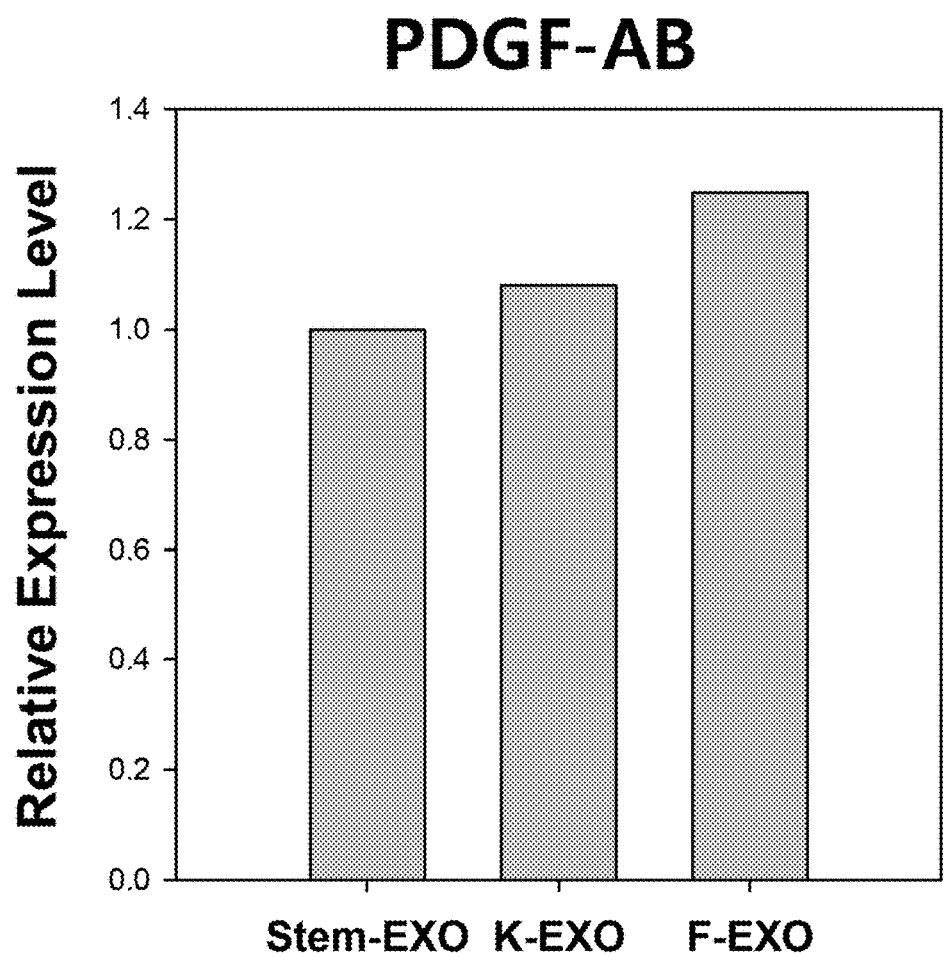
Figure 15C:
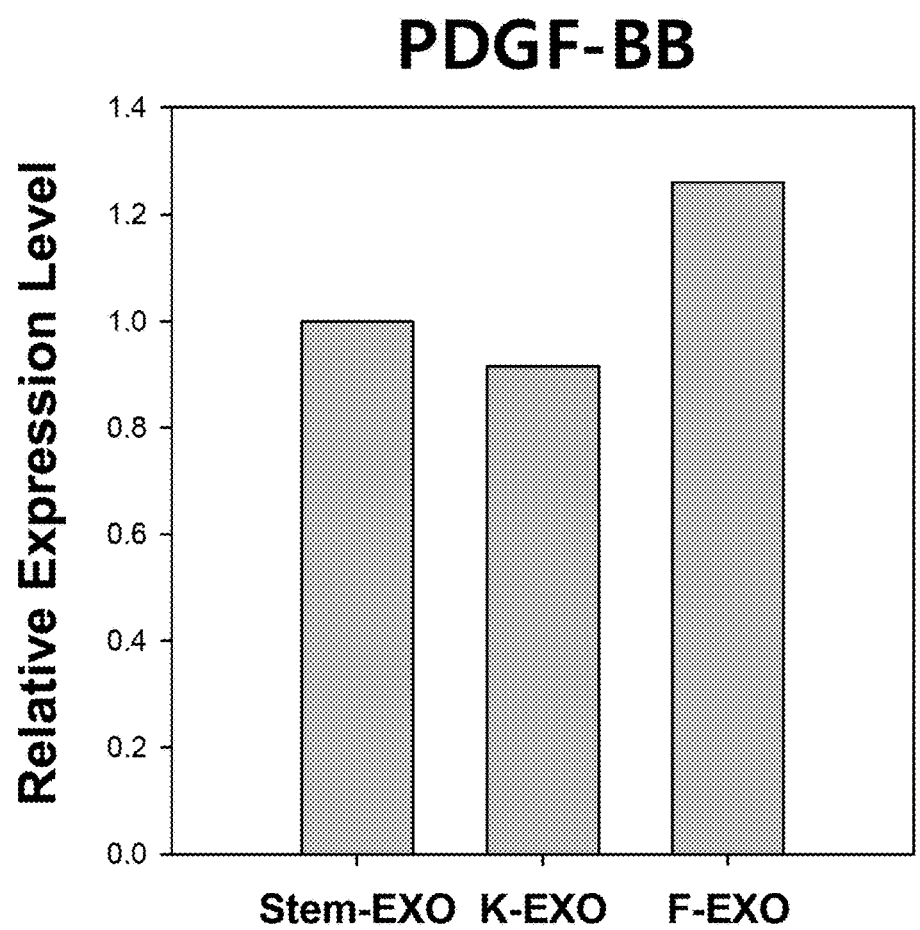
Figure 15D:
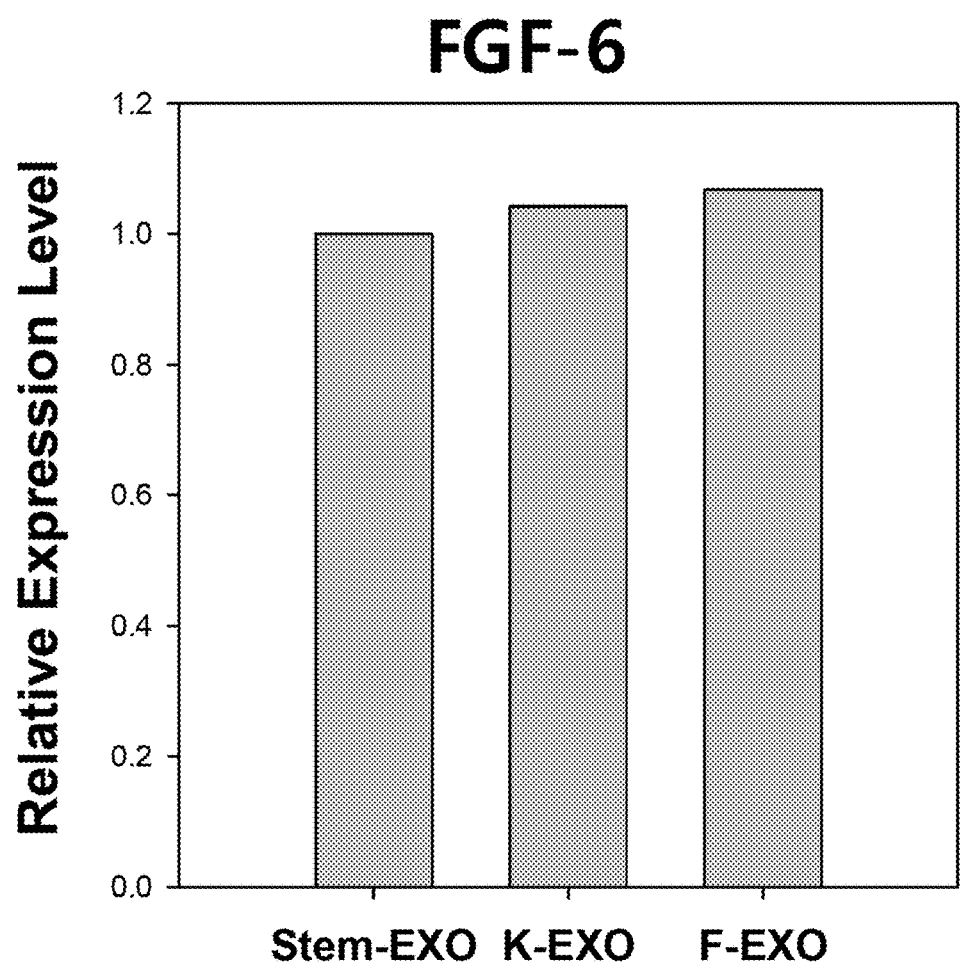
Figure 15E:
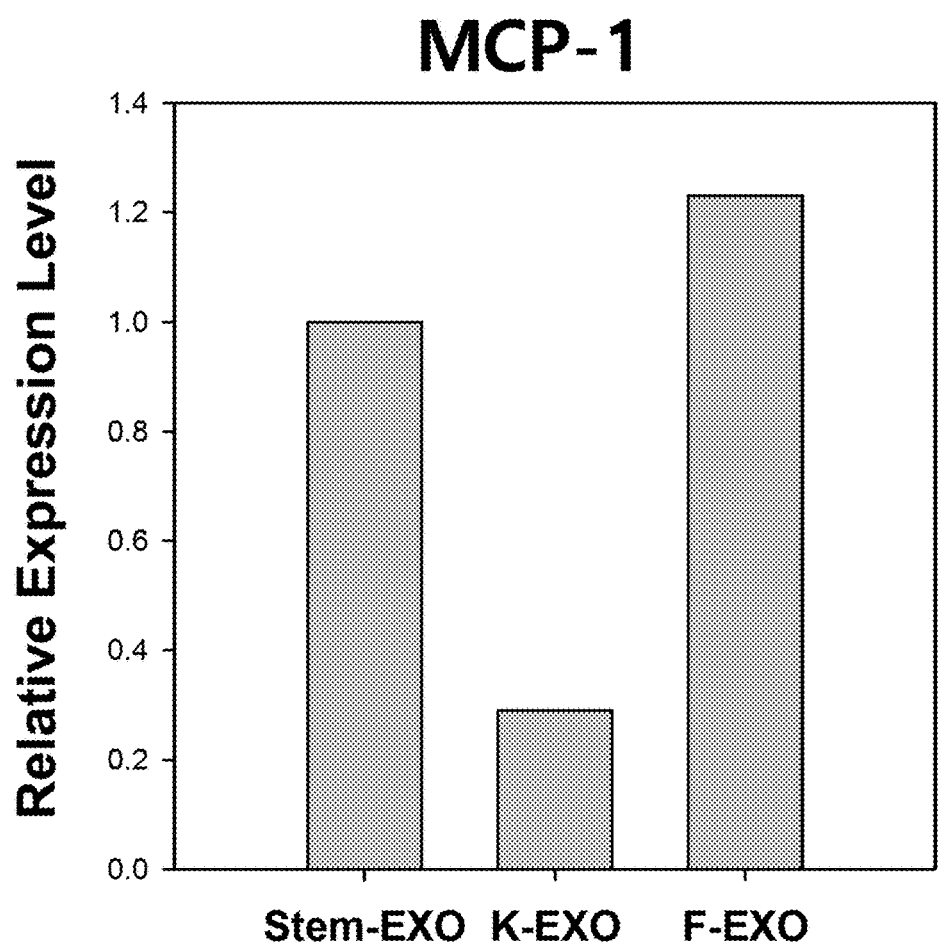
Figure 15F:
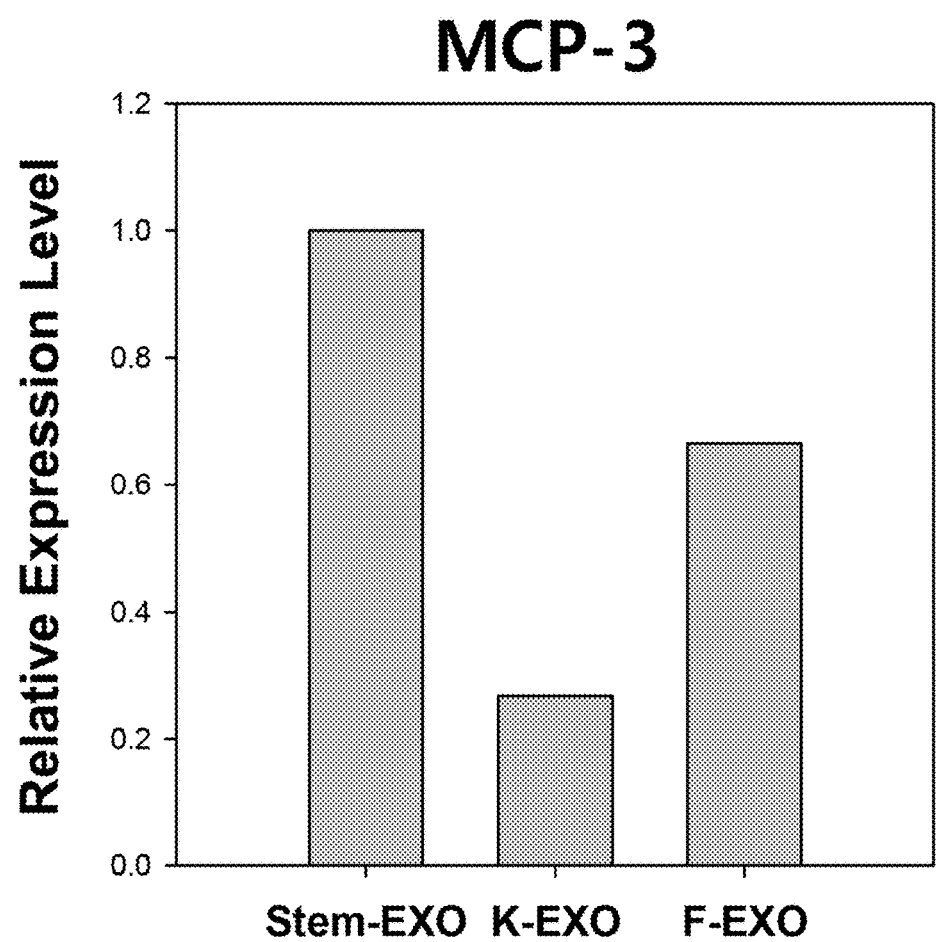
Figure 15G:
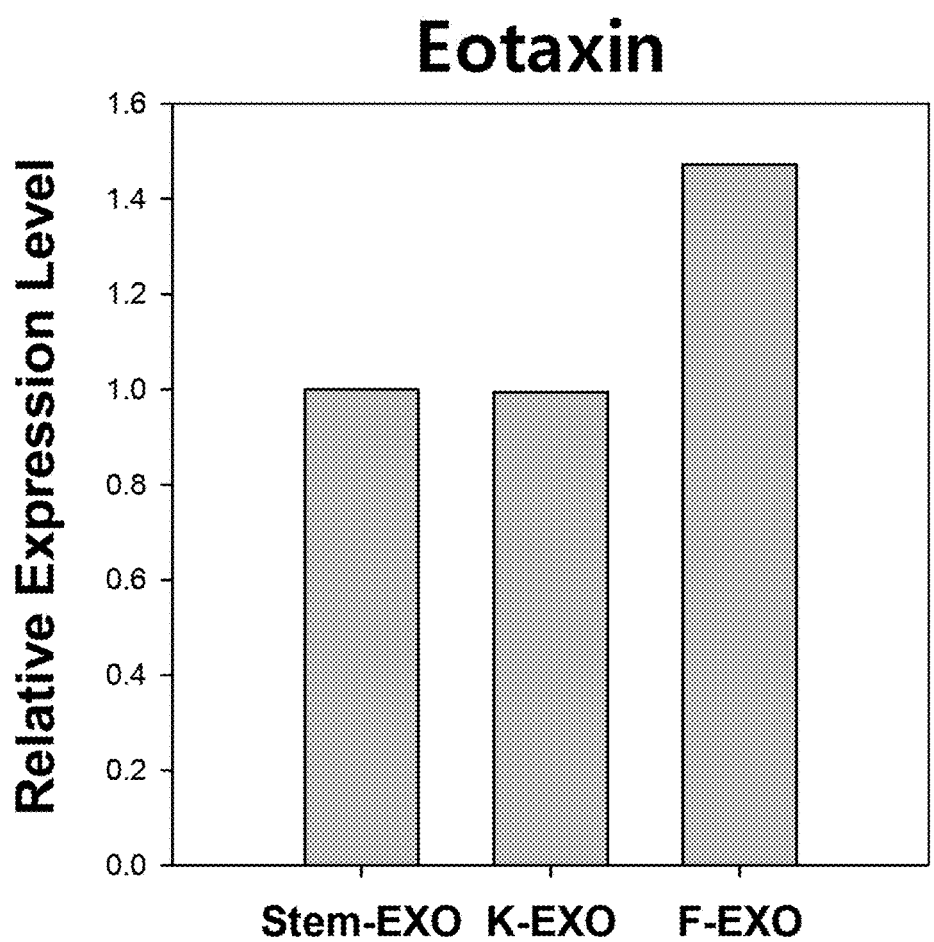
Figure 15H:
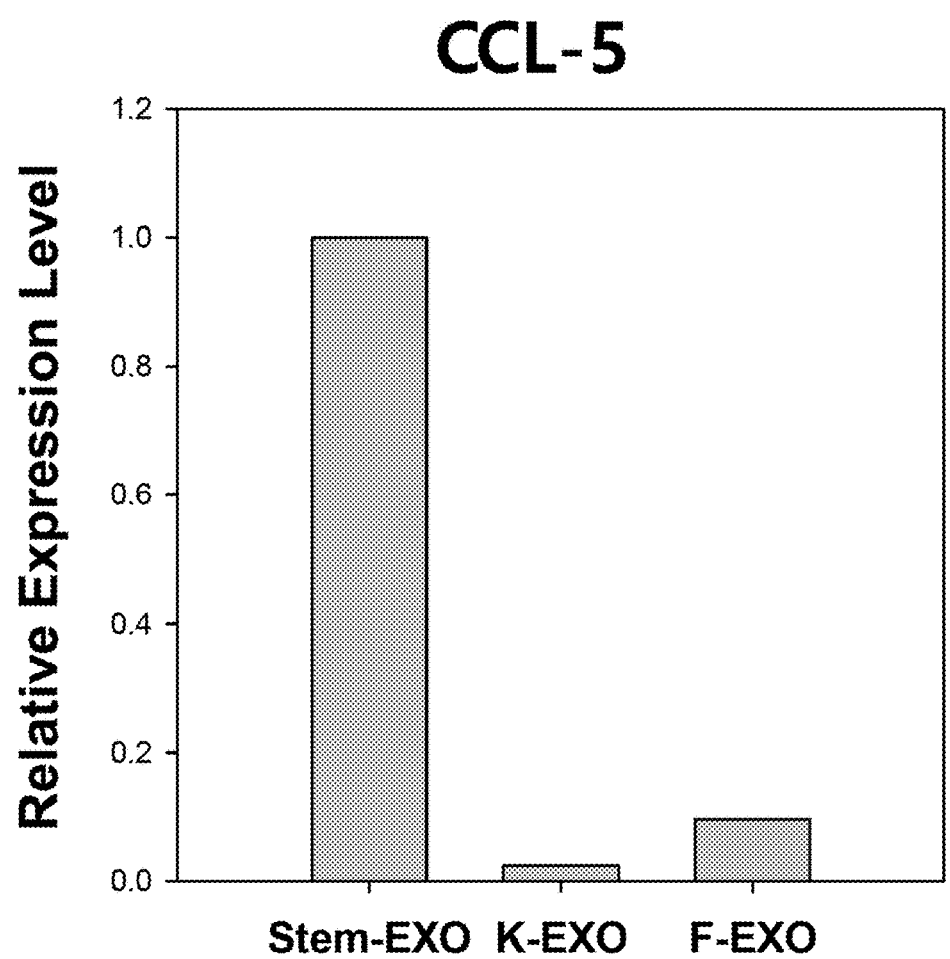
Figure 15I:
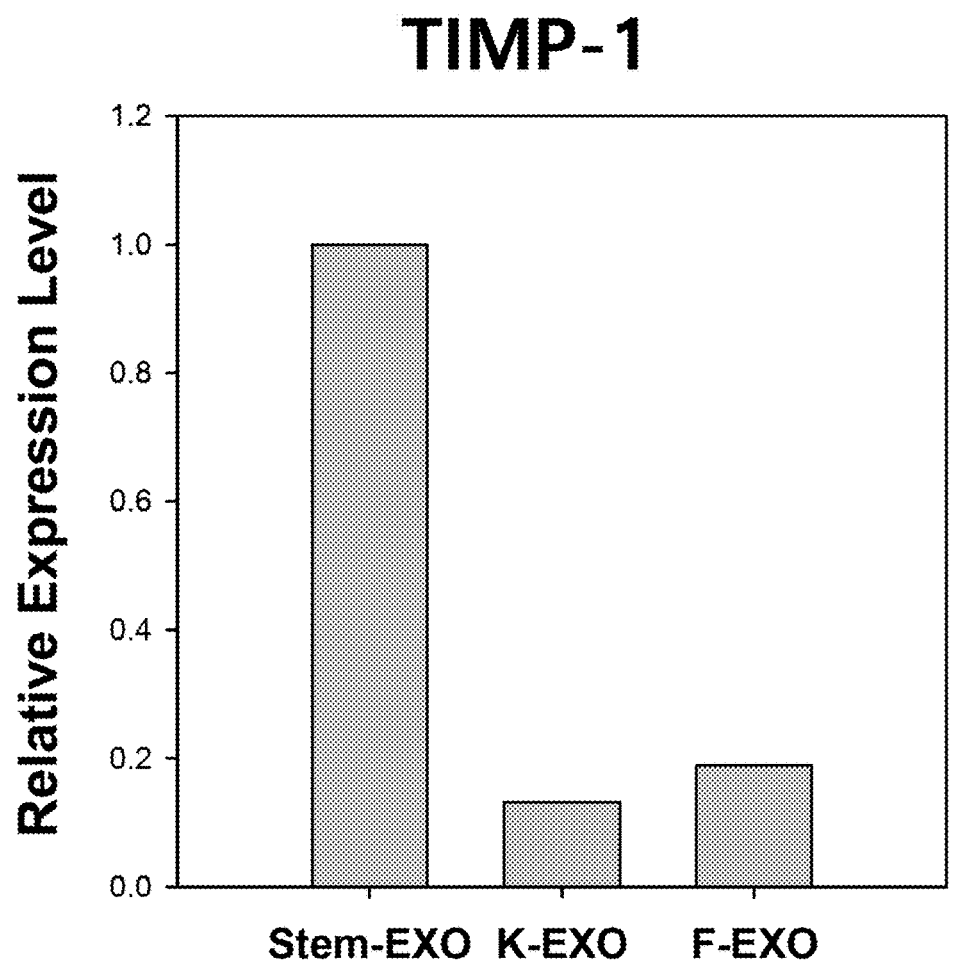
Figure 16A:
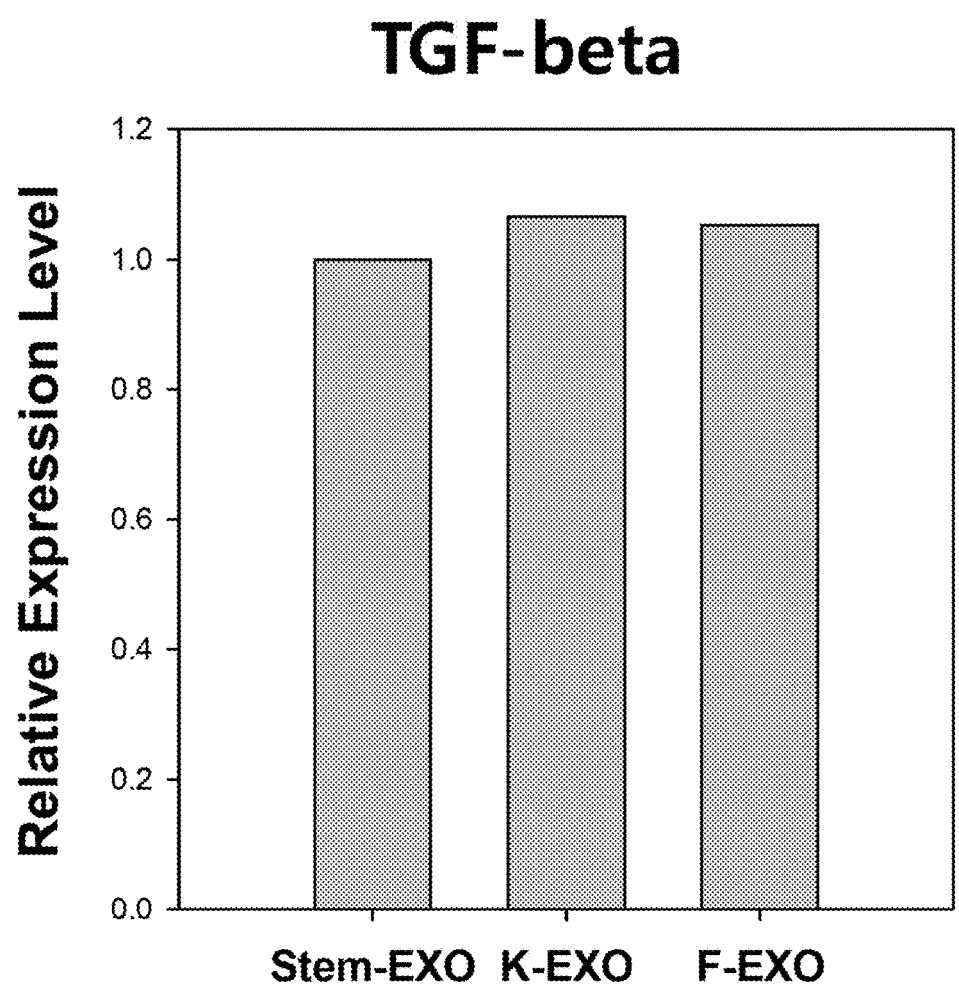
FIG. 16A to 16D shows graphs illustrating the expression level of bioactive factor (A: TGF-beta, B: TNF-alpha, C: IL-6, D: IL-8) related to whitening effect in the exosomes using g a microarray; Stem-EXO: exosomes derived from proliferating human adipose-derived stem cells, K-EXO: exosomes derived from human epidermal keratinocytes, F-EXO: exosomes derived from human foreskin fibroblasts.
Figure 16B:
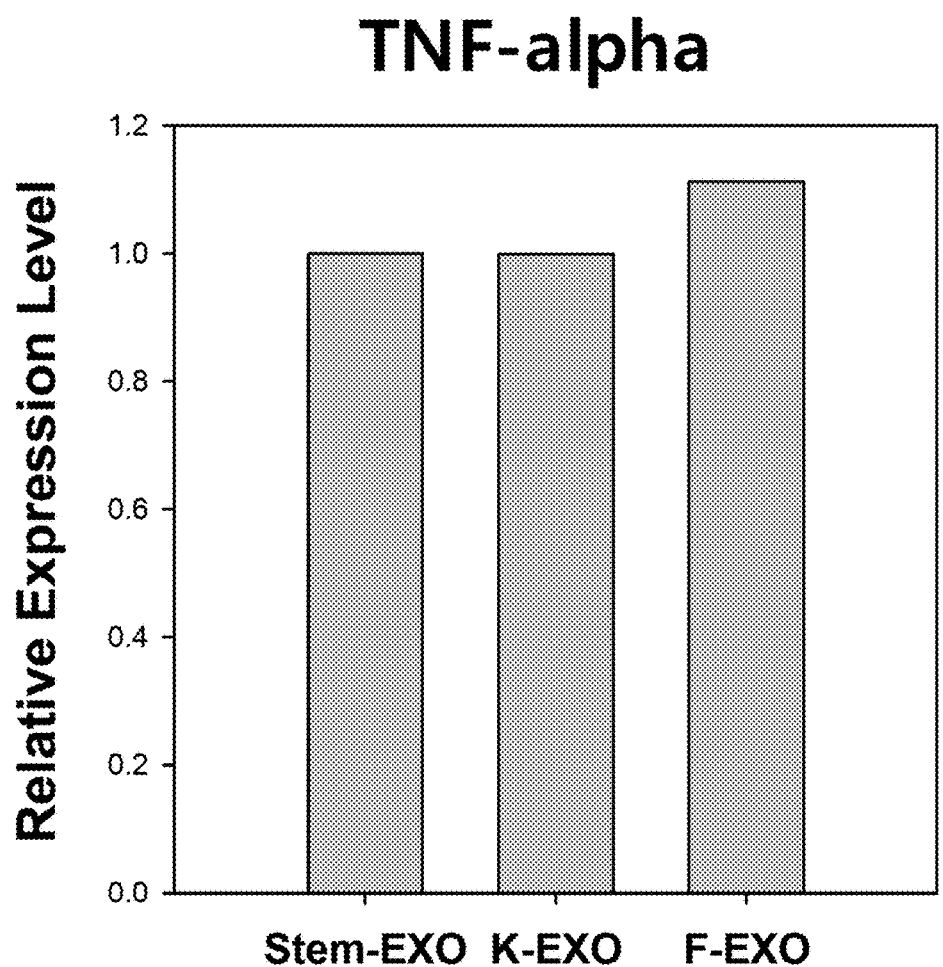
Figure 16C:
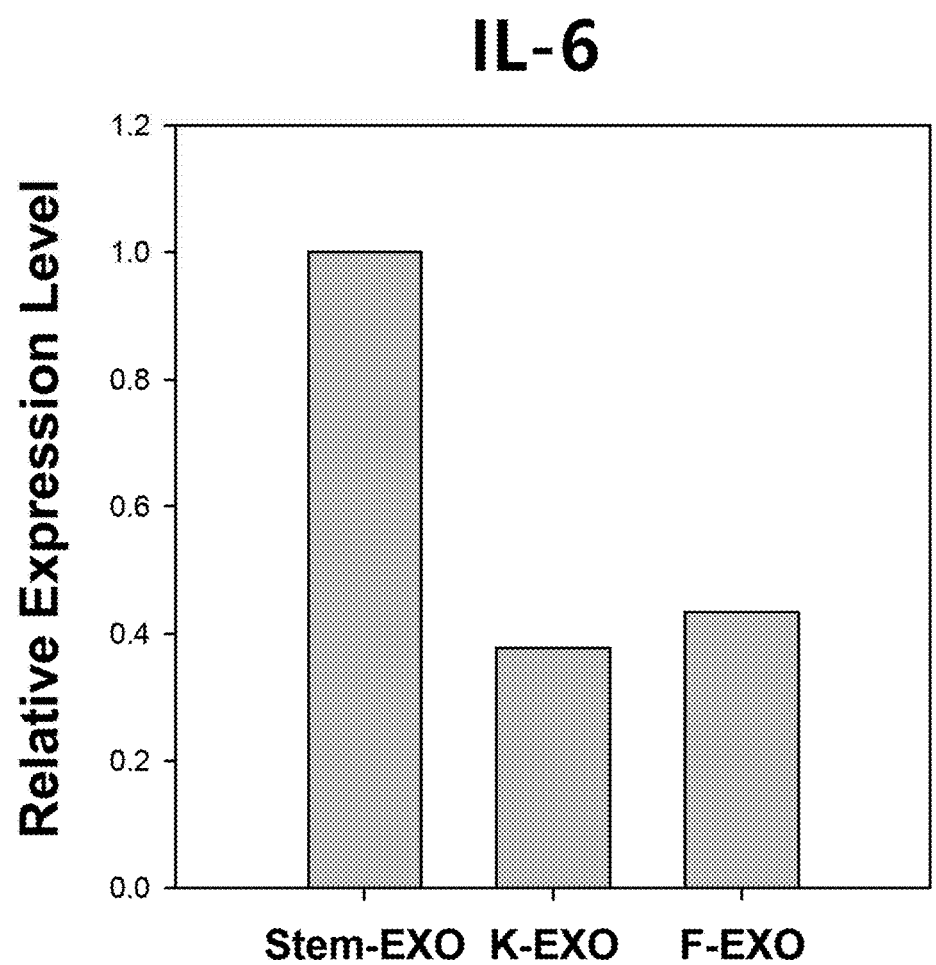
Figure 16D:
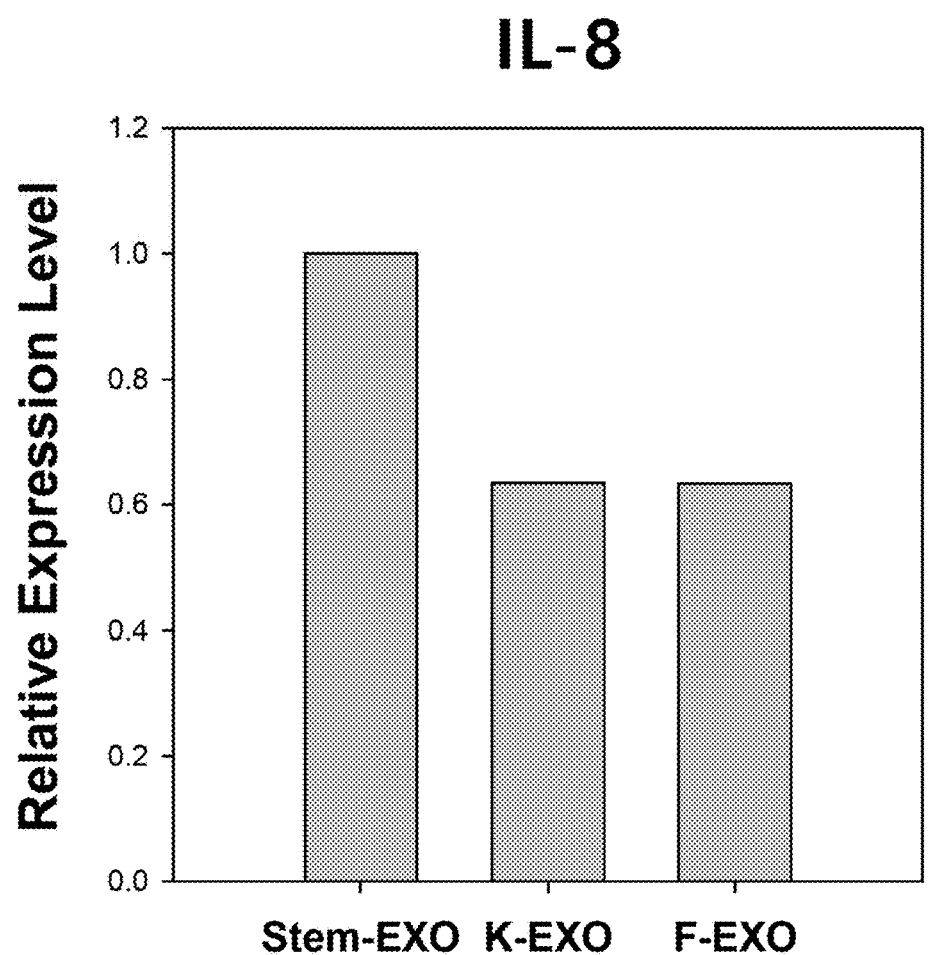
Figure 17A:
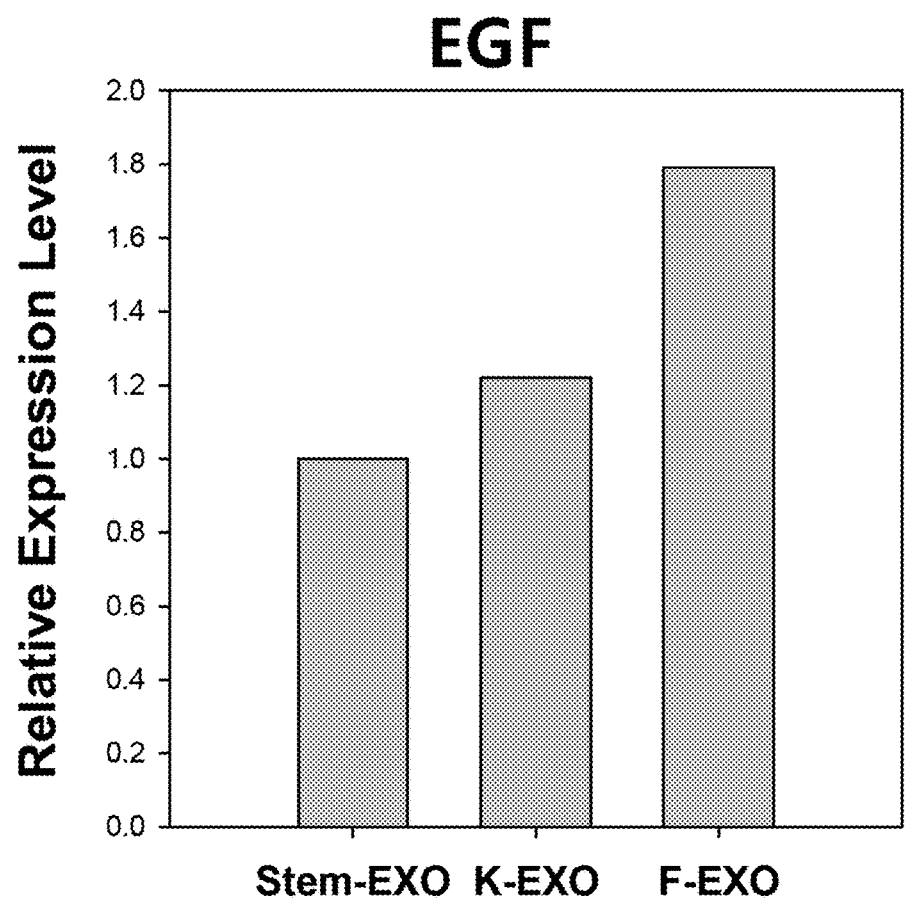
FIG. 17A to 17F shows graphs illustrating the expression levels of bioactive factors (A: EGF, B: HGF, C: PAI-1, D: VEGF, E: Angiogenin, F: Angiopoietin-1) related to skin regeneration and angiogenesis in the exosomes using a microarray; Stem-EXO: exosomes derived from proliferating human adipose-derived stem cells, K-EXO: exosomes derived from human epidermal keratinocytes, F-EXO: exosomes derived from human foreskin fibroblasts.
Figure 17B:
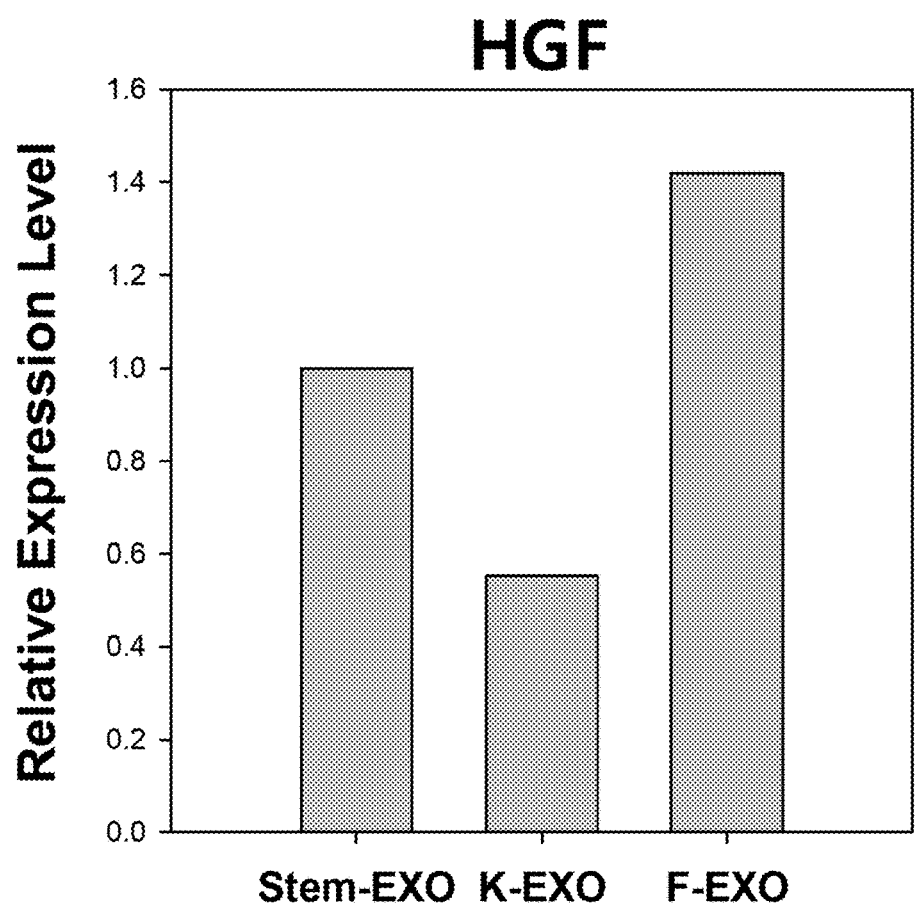
Figure 17C:
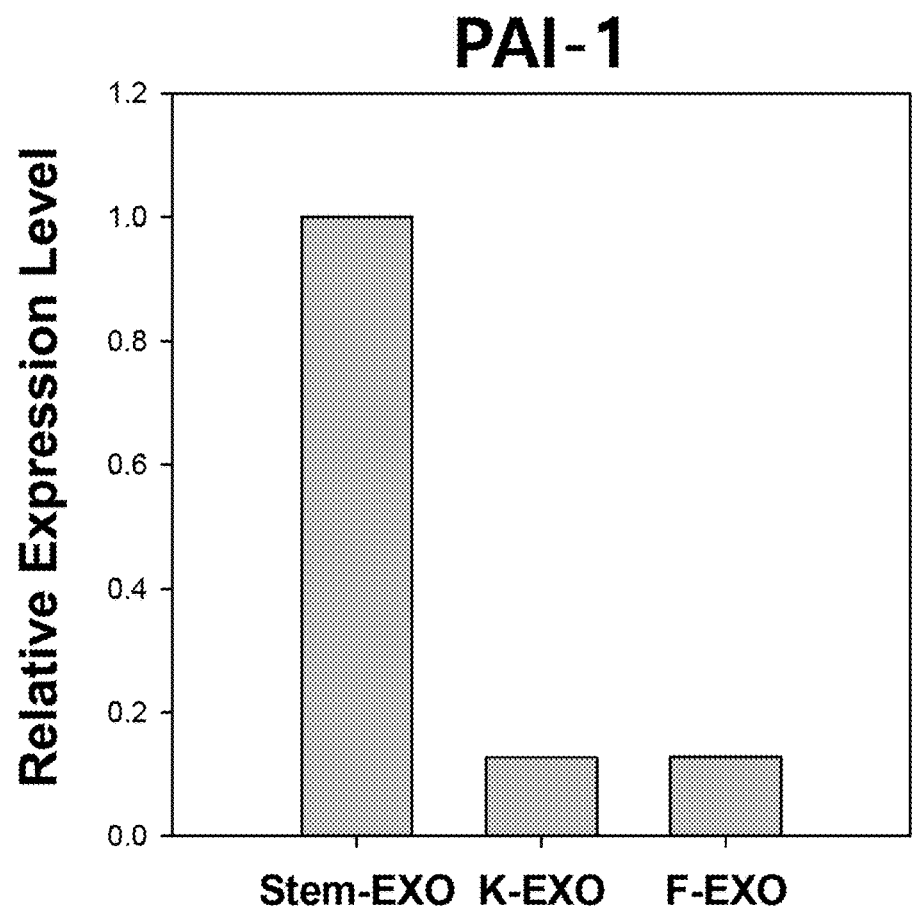
Figure 17D:
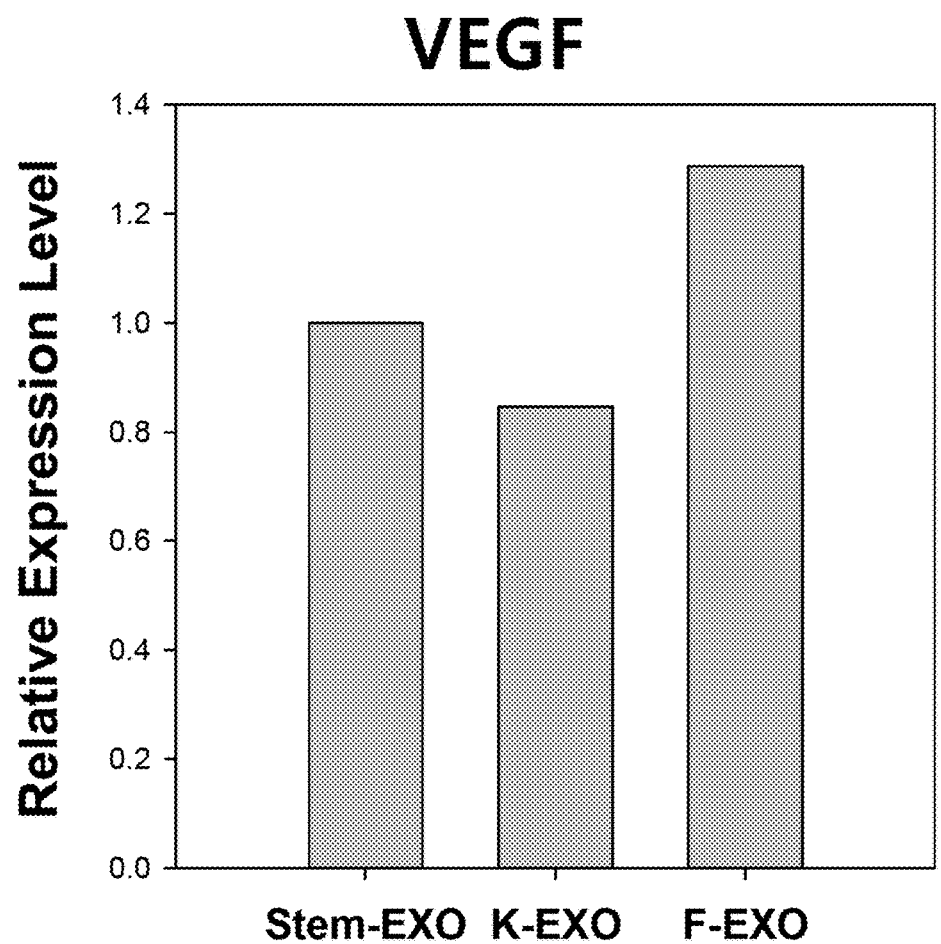
Figure 17E:
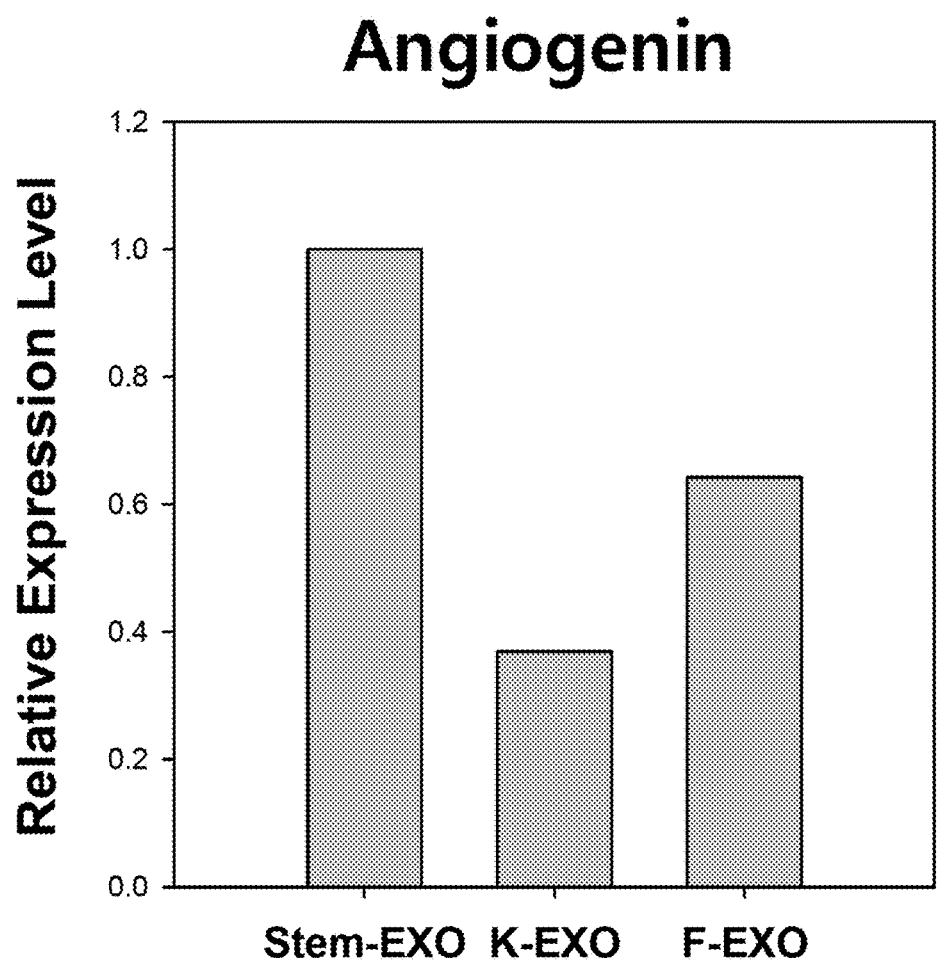
Figure 17F:
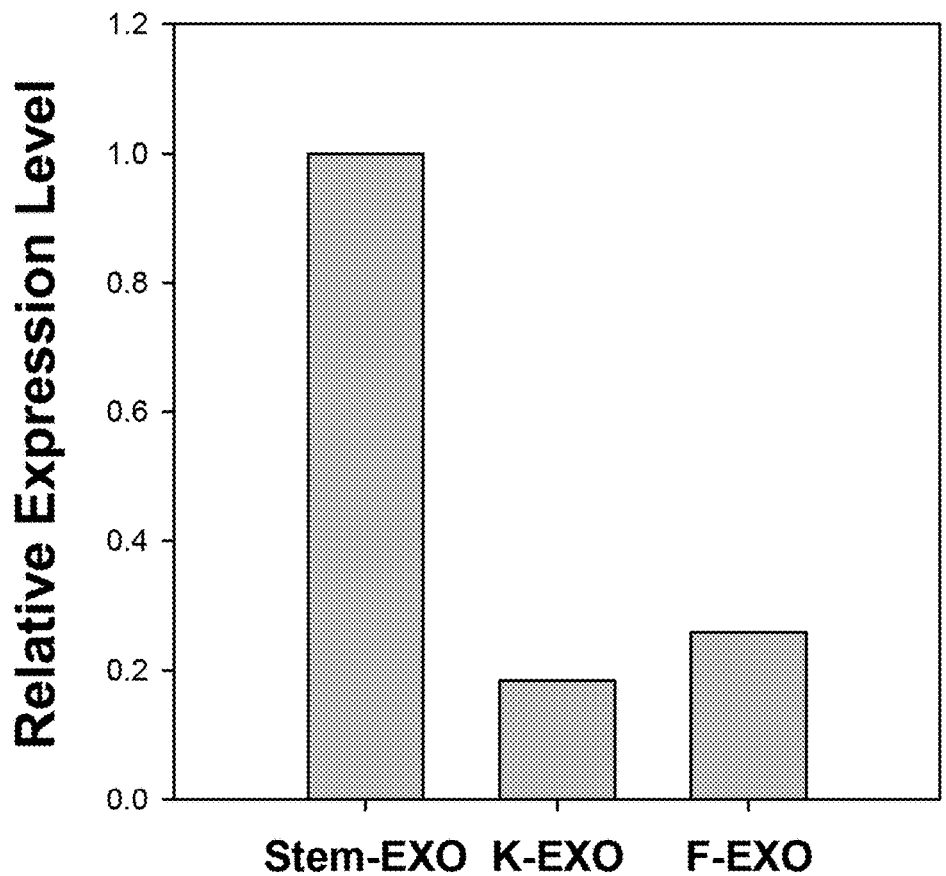

Through the microarray analysis, 9 bioactive factors influencing wrinkle improvement (PDFG-AA, PDGG-AB, PDGF-BB, FGF-6, MCP-1, MCP-3, Eotaxin, CCL-5, TIMP-1), 4 whitening-related bioactive factors (TGF-beta, TNF-alpha, IL-6, IL-8) and 6 bioactive factors related to skin regeneration and angiogenesis (EGF, HGF, PAI-1, VEGF, Angiogenin, Angiopoietin-1) were confirmed and in this regard, the relative expression levels of each bioactive factor in the exosomes derived from human adipose-derived stem cells and the exosomes derived from human epidermal keratinocytes and from human foreskin fibroblasts were compared (FIG. 14). FIGS. 14C and 14D show the relative expression levels of the bioactive factors, and the horizontal axis indicates the exosomes from human adipose-derived stem cells and the vertical axis indicates the exosomes from epidermal keratinocytes and fibroblast exosomes, respectively. In addition, the top line and the bottom line with the middle line of the graph at the center show 1.5-fold increase/decrease relative to the reference value, respectively. FIGS. 15A to 15I show the bioactive factors related to wrinkle improvement effect of the exosomes, FIGS. 16A to 16D show the bioactive factors related to whitening effect of the exosomes, and FIGS. 17A to 17F show the bioactive factors related to skin regeneration and angiogenesis of the exosomes.

As a result, as shown in FIGS. 15, 16 and 17, it was confirmed that there are different types of bioactive factors present in the exosomes derived from human adipose-derived stem cells (Stem-Exo), the exosomes derived from human epidermal keratinocytes (K-Exo) and the exosomes derived from human foreskin fibroblasts (F-EXO). Specifically, it was confirmed that the monocyte chemoattractant protein-1, -3 (MCP-1, -3), chemokine ligand 5 (CCL-5) and collagenase inhibitor (the tissue inhibitor of metalloproteinase-1 (TIMP-1)) related to the mechanisms associated with promoting collagen synthesis and inhibiting the degradation thereof, interleukin-6, -8 (IL-6, -8) associated with whitening, hepatocyte growth factor (HGF), palsminogen activator inhibitor-1 (PAI-1), angiogenin and angiopoietin-1 associated with skin regeneration and angiogenesis were overexpressed in the exosomes derived from human adipose-derived stem cells (Stem-EXO) compared to K-EXO and/or F-EXO (FIGS. 15, 16 and 17).

EXAMPLE 2-4

Effect on Migration Effect of Human Foreskin Fibroblasts Using Exosomes Derived from Proliferating Human Adipose-derived Stem Cells In order to examine the effect of the exosomes derived from human adipose-derived stem cells on the migration of human foreskin fibroblasts, medium compositions each containing the exosomes derived from the proliferating human adipose-derived stem cell (Stem-EXO), the exosomes derived from human epidermal keratinocytes (K-EXO) and the exosomes extracted from human foreskin fibroblasts (F-EXO) were used. Each of the medium compositions was prepared by adding Stem-EXO to a DMEM serum-free culture medium at concentrations of 10, 30 and 50 μg/mL, and adding K-EXO and F-EXO to a DMEM serum-free culture medium at a concentration of 50 μg/mL, respectively. The DMEM medium containing 10% serum was used as a positive control group and the DMEM serum-free medium was used as a negative control group. The human foreskin fibroblasts were labeled with green fluorescent dye, then seeded in a 24-well plate at $1 \times 10^5$ cells/well and cultured in a culture medium (DMEM containing 10% fetal bovine serum, 1% penicillin/streptomycin) for 72 hours. After culturing, an artificially uniform interval of wounds was prepared at the center of the bottom of the plate to which the cells were adhered using a sterilized yellow tip, and the medium compositions each containing the exosomes was applied to the cells.

Figure 18A:
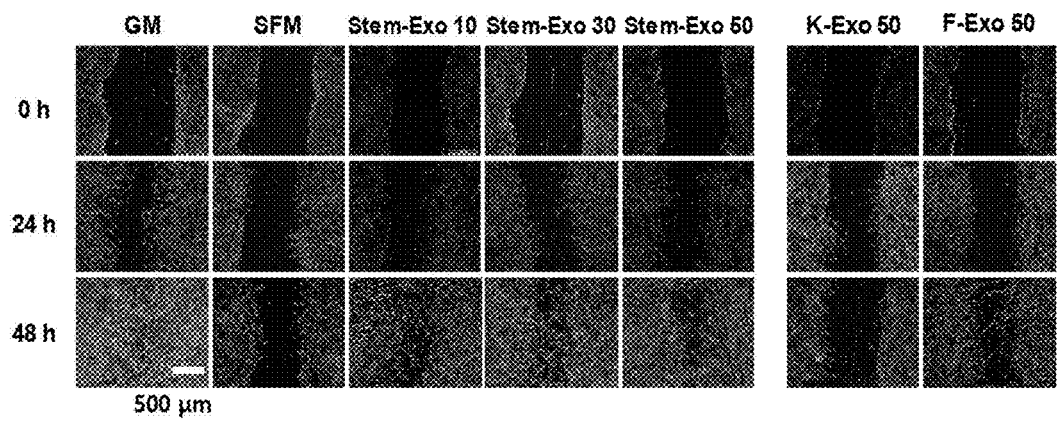
FIG. 18A to 18B shows diagrams illustrating the effect of human adipose-derived stem cell exosomes (Stem-EXO) on the migration of human fibroblasts; GM: stem cell culture medium (growth medium), SFM: serum-free medium, Stem-EXO: exosomes derived from proliferating human adipose-derived stem cells, K-EXO: exosomes derived from human epidermal keratinocytes, F-EXO: exosomes derived from human foreskin fibroblasts.
Figure 18B:
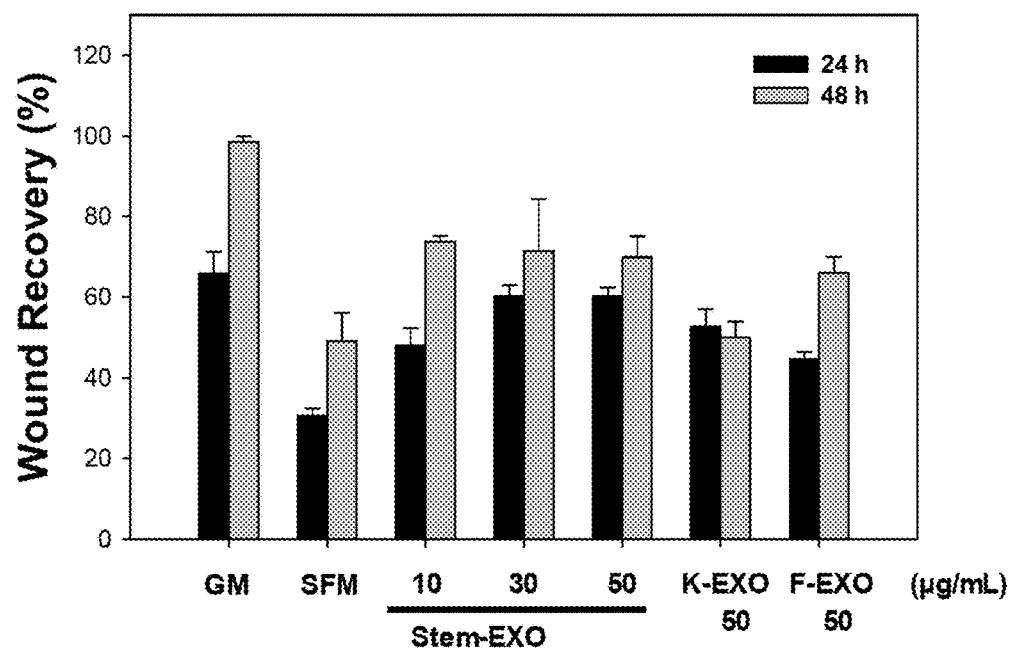

As a result, the cells treated with the medium containing Stem-EXO at 24 hours showed a higher degree of migration than the cells treated with negative control, K-EXO and F-EXO, and such tendency was even more prominent in the medium containing Stem-EXO at a concentration of 30 and 50 μg/mL. After 48 hours, the migration rapidly took place in the medium containing 10, 30 and 50 μg/mL of Stem-EXO, showing better (e.g., faster, having less scaring, or less discoloration) wound healing effect compared to the media containing K-EXO and F-EXO (FIGS. 18A and 18B).

Therefore, the exosomes derived from human adipose-derived stem cells (Stem-Exo) showed an excellent effect on the migration of human foreskin fibroblasts compared to K-EXO or F-EXO.

EXAMPLE 2-5

Effect of Exosomes Derived from Proliferating Human Adipose-derived Stem Cells on Wrinkle Improvement In order to examine the effect of the exosomes derived from human adipose-derived stem cells on the collagen synthesis of human foreskin fibroblasts, medium compositions each containing the exosomes derived from the proliferating human adipose-derived stem (Stem-EXO), the exosomes derived from human epidermal keratinocytes (K-EXO) and the exosomes derived from human foreskin fibroblasts (F-EXO) were used. The medium compositions each was prepared by adding Stem-EXO to a DMEM serum-free culture medium at concentrations of 10, 30 and 50 μg/mL, and adding K-EXO and F-EXO to a DMEM serum-free culture medium at a concentration of 50 μg/mL, respectively. The DMEM serum-free medium was used as a negative control group. The human foreskin fibroblasts were seeded in a 48-well plate at $5 \times 10^4$ cells/well and cultured in a culture medium (DMEM containing 10% fetal bovine serum, 1% penicillin/streptomycin) for 72 hours and then washed with PBS, and the medium compositions each containing the exosomes was applied to the cells.

After completion of culturing, the culture solution of each well was recovered, centrifuged at 25° C. at 3,000 rpm for 10 minutes, and then the supernatant was taken and used for the extraction and quantification of soluble collagen. Each well of the plate from which the culture solution had been removed was washed with PBS. Then the cells were separated from the bottom of each well by applying trypsin (trypsin-EDTA), and the number of cells was measured.

Sircol collagen assay kit (Biocolor, UK) was used for the quantification of soluble collagen. The thus-obtained supernatant was treated with Tris-HCl (pH 7.6) buffer mixed with polyethylene glycol and maintained at 4° C. for 12 hours or more. Thereafter, the resultant was centrifuged at 12,000 rpm for 10 minutes to concentrate collagen. After removing the supernatant, 1 mL of the provided collagen adsorption dye (sircol dye reagent) was added to the collagen pellet and then cultured with shaking for 30 minutes. The unadsorbed dye was removed by centrifugation at 12,000 rpm for 10 minutes, and the pellet was washed with an acid salt buffer. Then the dye adsorbed on the collagen was dissolved by applying an alkali reagent, and the absorbance was measured at a wavelength of 555 nm. The absorbance was substituted into the equation of the standard curve to calculate the amount of soluble collagen in the wells to which Stem-EXO, K-EXO, F-EXO and the negative control substance were added, respectively. The calibrated amount of collagen was substituted into the equation to calculate the synthesis rate.

Figure 19:
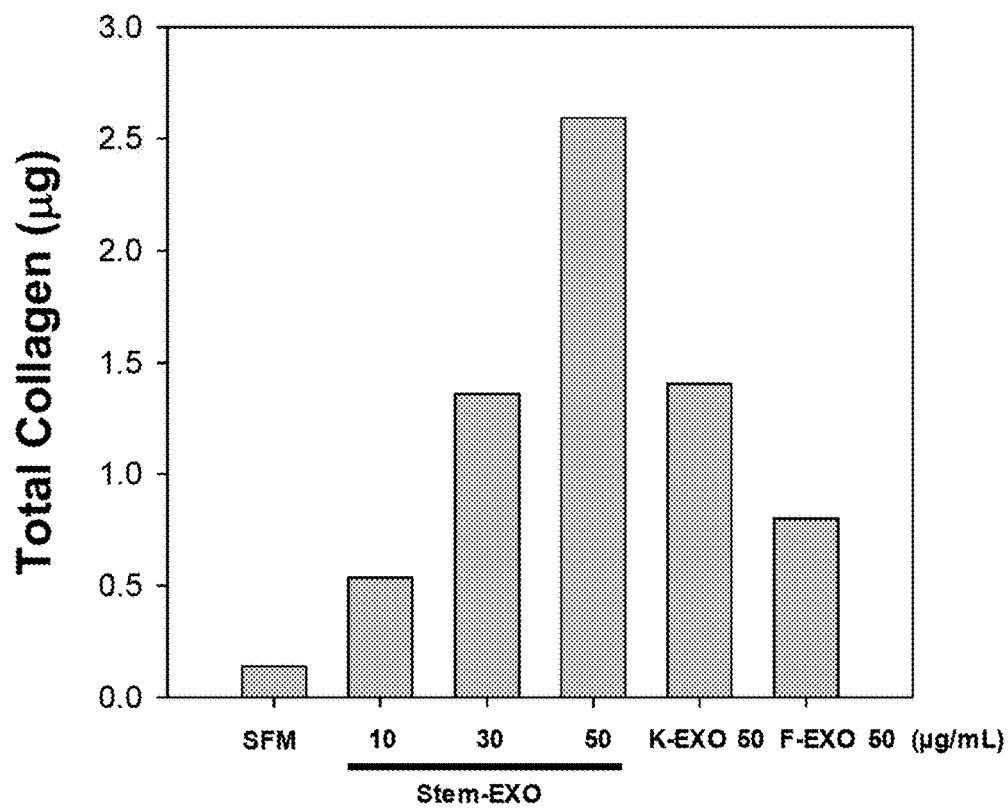
FIG. 19 shows a graph illustrating the effect of human adipose-derived stem cell exosomes (Stem-EXO) on collagen synthesis of human fibroblasts; SFM: serum-free medium, Stem-EXO: exosomes derived from proliferating human adipose-derived stem cells, K-EXO: exosomes derived from human epidermal keratinocytes, F-EXO: exosomes derived from human foreskin fibroblasts.

As a result, the soluble collagen synthesis rate for the group treated with Stem-EXO increased depending on the concentration of the exosome used, compared with the negative control group (0.138 μg). Specifically, in the case of the group treated with Stem-EXO at 50 μg/mL, the amount of collagen synthesis was 2.59 μg, which was significantly increased compared to the same amount of K-EXO (1.4 μg) or F-EXO (0.8 μg). Therefore, it can be implied that the exosomes derived from human adipose-derived stem cells has the effect of promoting collagen synthesis of human foreskin fibroblasts (FIG. 19).

EXAMPLE 2-6

Inhibitory Effect of Exosomes Derived from Proliferating Human Adipose-Derived Stem Cells on Melanin Production Using Mouse Melanoma The whitening effect of the exosomes derived from human adipose-derived stem cells (Stem-EXO), and the exosomes derived from human epidermal keratinocytes (K-EXO) and the exosomes derived from human foreskin fibroblasts (F-EXO) as control groups were determined by the degree of inhibition of melanin production in mouse melanoma. The melanoma cells are cells that are derived from mouse melanoma and secrete a melanin pigment referred to as "melanin" The melanoma cells were seeded at a density of $1 \times 10^5$ cells/well in a 96-well plate to adhere the cells, and then cultured for 3 days by replacing the culture medium with a medium containing Stem-EXO, K-EXO and F-EXO, respectively. After 3 days, the medium was recovered and centrifuged at 4,500 rpm for 10 minutes, and the absorbance was measured at 405 nm to calculate the amount of melanin released from the cells. The cells adhered to the plate were removed by applying trypsin (trypsin-EDTA), and the number of cells was measured, followed by centrifugation to recover the cells. The cells were washed once with PBS and centrifuged to obtain cell pellets. To the cell pellets, 1 ml of 1 N sodium hydroxide (NaOH) solution containing 10% dimethyl sulfoxide (DMSO) was added to dissolve the melanin at 80° C. for 2 hours, then the resultant was added to a 96-well plate, and the absorbance was measured at 405 nm. The melanin was quantified using the measured absorbance and normalized to the protein concentration of the sample to determine the concentration of the synthesized melanin.

Figure 20:
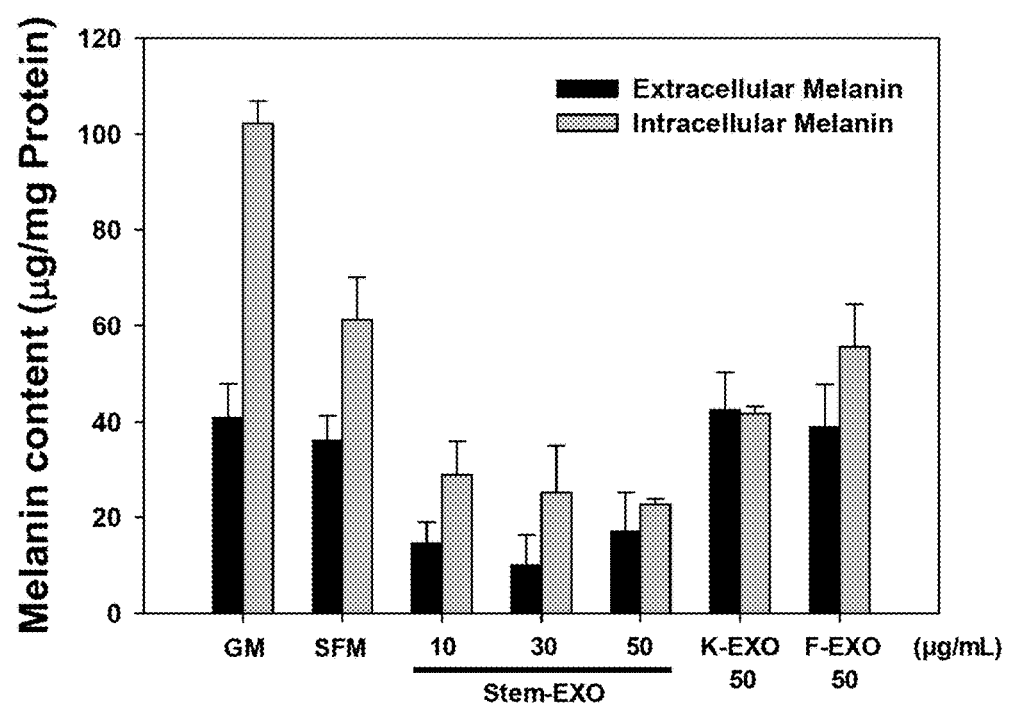
FIG. 20 shows a graph illustrating the effect of human adipose-derived stem cell exosomes (Stem-EXO) on the melanin synthesis of mouse melanocytes; GM: stem cell culture medium (growth medium), SFM: serum-free medium, Stem-EXO: exosomes derived from proliferating human adipose-derived stem cells, K-EXO: exosomes derived from human epidermal keratinocytes, F-EXO: exosomes derived from human foreskin fibroblasts.

The exosomes derived from human adipose-derived stem cells were used on the melanoma cells at a concentration of 10, 30 and 50 μg/mL, and the degree of melanin synthesis was examined. As a result, it was confirmed that the melanin synthesis was reduced at all concentrations of the exosomes derived from stem cells (FIG. 20).

EXAMPLE 2-7

Cosmetic Compositions Containing Exosomes Derived from Proliferating Human Adipose-derived Stem Cells According to Example 2-1, a liposome encapsulating the exosomes and derived from the proliferating human adipose-derived stem cells was prepared.

Specifically, 3% by weight of lecithin was dispersed in an aqueous phase containing 0.01% by weight of the exosomes derived from the proliferating stem cells at room temperature (15° C.), and then a reverse micelle emulsion (water/low-temperature process carbon dioxide) was prepared using supercritical carbon dioxide. Subsequently, the reaction was terminated, the supercritical carbon dioxide was vaporized under reduced pressure to remove the supercritical carbon dioxide phase, and a low-temperature process liposome suspension, in which the exosomes derived from the proliferating stem cells encapsulated, was obtained. Here, the temperature of the reaction process was 4° C. or below.

The cosmetic composition was prepared by the composition shown in Table 3 below using the liposome encapsulating the exosomes.

TABLE 3

| Composition | Content (% by weight) |
| --- | --- |
| Stearic acid | 2 |
| Cetyl alcohol | 2 |
| Lanolin alcohol | 2 |
| Liquid paraffin | 7 |
| Cyclomethicone | 5 |
| Polyoxyethylene monooleic acid ester | 2 |
| Hexanediol | 2 |
| Glycerin | 3 |
| Triethylamine | 5 |
| Carbomer | 0.2 |
| Liposome encapsulating the exosomes according to Example 2-1 of the present invention | 0.01 |
| Purified water | remainder |

FORMULATION EXAMPLE 1

Preparation of Skin Softening Cosmetic Water (Skin Lotion)

The skin softening cosmetic water (skin lotion) was prepared by the composition shown in Table 4 below using the liposome encapsulating the exosomes derived from the proliferating stem cells obtained by the method of Example 2-7.

TABLE 4

| Composition | Content (% by weight) |
| --- | --- |
| Liposome encapsulating the exosomes according to Example 2-1 of the present invention | 0.01 |
| Ethanol | 10 |
| Glycerin | 3 |
| Butylene glycol | 3 |
| Sodium hyaluronate | 0.1 |
| Triethanolamine | 0.1 |
| Antioxidants | 0.1 |
| Preservatives, flavoring, coloring | 0.1 |
| Purified water | remainder |

FORMULATION EXAMPLE 2

Preparation of Nutritive Cosmetic Water (Milk Lotion)

The nutritive cosmetic water (milky lotion) was prepared by the composition shown in Table 5 below using the liposome encapsulating the exosomes derived from the proliferating stem cells obtained by the method of Example 2-7.

TABLE 5

| Composition | Content (% by weight) |
| --- | --- |
| Liposome encapsulating the exosomes according to Example 2-1 of the present invention | 0.01 |
| Glycerin | 5 |
| Mineral oil | 4 |
| Beeswax | 4 |
| Polysorbate-60 | 1.5 |
| Carboxyvinyl polymer | 0.1 |
| Butylene glycol | 3 |
| Squalane | 5 |
| Triethanolamine | 0.15 |
| Preservatives, flavoring, coloring | 0.1 |
| Purified water | remainder |

What is claimed is:

1. A method for skin whitening, wrinkle improvement, skin regeneration, or a combination thereof, the method comprising:
    preparing exosomes derived from stem cells comprising proliferating stem cells;
    whitening skin of a subject, improving wrinkles of the subject, regenerating the skin of the subject, or a combination thereof, by administering the exosomes to the subject,
    wherein the exosomes are derived from stem cells differentiating into adipocytes.

2. The method of claim 1, wherein the stem cells comprise one or more of bone marrow stem cells, cord blood stem cells, or adipose-derived stem cells.

3. The method of claim 2, wherein the stem cells are human-derived or animal-derived stem cells.

4. The method of claim 1, wherein the administering the exosomes to the subject comprises administering the exosomes to the subject at a concentration of 1 to 150 µg per 1 mL of a composition comprising the exosomes.

5. The method of claim 1, wherein whitening skin of the subject, improving wrinkles of the subject, regenerating the skin of the subject, or the combination thereof includes whitening the skin of the subject.

6. The method of claim 1, wherein whitening skin of a subject, improving wrinkles of the subject, regenerating the skin of the subject, or the combination thereof includes reducing the wrinkles of the subject.

7. The method of claim 1, wherein whitening skin of a subject, improving wrinkles of the subject, regenerating the skin of the subject, or the combination thereof includes regenerating the skin of the subject.

8. A method for skin whitening, wrinkle improvement, skin regeneration, or a combination thereof, the method comprising:
    preparing exosomes derived from stem cells comprising proliferating stem cells;
    whitening skin of a subject, improving wrinkles of the subject, regenerating the skin of the subject, or a combination thereof, by administering the exosomes to the subject,
    wherein the stem cells are adipose-derived stem cells.

9. The method of claim 8, wherein the stem cells are human-derived or animal-derived stem cells.

10. The method of claim 8, wherein the administering the exosomes to the subject comprises administering the exosomes to the subject at a concentration of 1 to 150 µg per 1 mL of a composition comprising the exosomes.

11. The method of claim 8, wherein whitening skin of the subject, improving wrinkles of the subject, regenerating the skin of the subject, or the combination thereof includes whitening the skin of the subject.

12. The method of claim 8, wherein whitening skin of a subject, improving wrinkles of the subject, regenerating the skin of the subject, or the combination thereof includes reducing the wrinkles of the subject.

13. The method of claim 8, wherein whitening skin of a subject, improving wrinkles of the subject, regenerating the skin of the subject, or the combination thereof includes regenerating the skin of the subject.

* * * * *